(12) United States Patent
Albers et al.

(10) Patent No.: US 7,208,077 B1
(45) Date of Patent: Apr. 24, 2007

(54) SENSOR ARRANGEMENT WITH ELECTRICALLY CONTROLLABLE ARRAYS

(75) Inventors: Joerg Albers, Brokdorf (DE); Helmut Bernt, Berlin (DE); Reinhard Bredehorst, Hamburg (DE); Rainer Hintsche, Berlin (DE); René Seitz, Itzehoe (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/958,633

(22) PCT Filed: Apr. 14, 2000

(86) PCT No.: PCT/EP00/03404

§ 371 (c)(1),
(2), (4) Date: Mar. 22, 2002

(87) PCT Pub. No.: WO00/62048

PCT Pub. Date: Oct. 19, 2000

(30) Foreign Application Priority Data

Apr. 14, 1999 (DE) ................................ 199 16 921
Jul. 12, 1999 (WO) ...................... PCT/EP99/04883

(51) Int. Cl.
*G01N 27/403* (2006.01)
*G01N 27/327* (2006.01)

(52) U.S. Cl. ............ 205/782; 204/403.14; 204/403.01; 204/409

(58) Field of Classification Search ................. 204/194, 204/400, 403.01, 403.03, 403.04, 403.13, 204/403.14, 406, 409; 435/4, 7.1; 205/777.5, 205/782

See application file for complete search history.

(56) References Cited

U.S. PATENT DOCUMENTS

| 4,225,410 | A | * | 9/1980 | Pace ........................ 204/412 |
| 5,120,421 | A | | 6/1992 | Glass et al. |
| 5,605,662 | A | | 2/1997 | Eugene et al. |
| 5,653,939 | A | * | 8/1997 | Hollis et al. .................. 422/50 |
| 5,670,031 | A | | 9/1997 | Hintsche et al. |
| 5,965,452 | A | | 10/1999 | Kovacs |

(Continued)

FOREIGN PATENT DOCUMENTS

EP          0 455 508 A1    3/1991

(Continued)

OTHER PUBLICATIONS

"Rapid determination of single base mismatch mutations in DNA hybrids by direct electric field Control", R.G. Sosnowski, Et Al., *Proc.Natl.Acad.Sci, U.S.A.*, Feb. 1997, vol. 94, pp. 1119-1123; XP000857636.

(Continued)

*Primary Examiner*—Alex Noguerola
(74) *Attorney, Agent, or Firm*—Duane Morris LLP

(57) ABSTRACT

An electric sensor array which is provided with several sensor positions that each have at least two microelectrodes. Molecular substances can be detected electrochemically and charged molecules can be transported or handled using the array. Measuring procedures can be effected, especially using two addressing procedures, in which sensor positions can be individually addressed and electrochemically or electrically controlled by pairing or in groups for voltage or impedance measurements. For biomolecular assays, affinity-binding molecules can be immobilized at the sensor positions, between the microelectrodes, or on auxiliary surfaces.

41 Claims, 11 Drawing Sheets

U.S. PATENT DOCUMENTS

| | | | |
|---|---|---|---|
| 6,083,366 A | 7/2000 | Higson | 204/203 |
| 6,225,059 B1 * | 5/2001 | Ackley et al. | 435/6 |
| 6,485,703 B1 * | 11/2002 | Cote et al. | 424/9.1 |
| 6,762,050 B2 * | 7/2004 | Fukushima et al. | 435/287.9 |

FOREIGN PATENT DOCUMENTS

| | | |
|---|---|---|
| WO | WO 95/26500 | 10/1995 |
| WO | WO 96/33403 | 10/1996 |
| WO | WO 98 01758 A | 1/1998 |
| WO | WO 99/07879 | 2/1999 |

OTHER PUBLICATIONS

"*Highly Sensitive and Selective Voltammetric Detection of Dopamine with Vertically Separated Intedigitated Array Electrodes*", O. Niwa, Et Al., Electroanalysis, 3 (1991) p. 163-168. XP000863401.

* cited by examiner

SENSOR ARRANGEMENT WITH ELECTRICALLY CONTROLLABLE ARRAYS

This application is a 371 of PCT/EP00/03404, filed Apr. 14, 2000, which claims priority from DE 19916921.7, filed Apr. 14, 1999, and PCT/EP99/04883, filed Jul. 12, 1999.

FIELD OF INVENTION

The invention relates to an electric sensor array and methods using multiple ultramicroelectrodes as electrochemical transducers and to be used as a component of measuring arrangements for simultaneously detecting different molecules from mixtures of substances in biochemical analytics, medical diagnostics and environmental control. The invention also relates to methods for improving analytic processes.

BACKGROUND OF THE INVENTION

For an analysis of biochemical assays it is desired to detect several analytes simultaneously in so-called array arrangements. Such arrays are widely known on the basis of optical detection. It would advantageous to record electric measuring signals directly, and not indirectly over optical detection means, and to measure particle-tolerantly and independently of the volume. An electric detection would provide cost advantages and a tougher handling.

Starting out from classic electrode systems for electrochemical detection, considerable efforts have been made to miniaturize electrodes. The term usually designates electrochemically used electrode structures having dimensions of less than 5 μm. Wightman and Dipf describe possibilities of voltammetry at ultramicroelectrodes in Electroanalytical Chemistry, Ed. A. J. Bard (Marcel Dekker, New York 1988) vol. 15, p. 267.

Ultramicroelectrodes of this type also allow particular detection methods, such as redox recycling, compare Niwa et al., Electroanalysis 3(1991) 163–168, said method being particularly advantageously applied for biochemical affinity assays with enzyme marking, such as they are general practice in immuno and DNA assays. Electrode structures having a structural width of below 300 nm permit a marker-free detection of the affinity binding of large molecules to electrode-bound catcher molecules by using impedance spectroscopy, compare also DE-A 196 10 115.

A pair of planar interdigital electrodes for conductometric and voltammetric measurements is designated as array by Sheppard et al. in Anal. Chem., 65(1993) 1202.

Tang et al. Anal. Chimica Acta, 214 (1988) 187 suggest an individual interdigital electrode pair as a detector system for an immunoassay consisting of an antigen and an antibody.

However, all said arrangements have only been described with respect to an individual analyte determination, not allowing an individual electric detection of array-typical different molecule species.

Microelectrode arrays having 16 parallel strip electrodes and an electrode width of 0.1 mm have been described by Aoki et al., Anal. Chem. 64 (1992) 44 for an electrochemical detection. According thereto, different polarization voltages are applied at said individual strip electrodes and maintained constant. The electrodes are read out serially in msec cycles, without switches being allocated to said individual electrodes. A low-pass filter prevents the occurrence of charging currents. Said arrangement only provides a detection of individual or different electrode-active species in solution.

DE 4318519 describes an advancement of pairs of interdigital electrodes to an array having multiple interdigital electrodes for a simultaneous use at a multipotentiostat. According to said method, the potentials at said electrodes are individually controlled and kept constant. Said array is also only suited for a simultaneous and parallel measurement of an analyte in solution. Also having a multipotentiostat, 4 fields having dot-shaped microelectrodes in parallel for determining different metals by an anodic stripping method have been described, cf. DE 44 24 355 C2. The method only allows the particular stripping voltammetry as a detection method, voltage ramps having been modulated by a square-wave-voltammetry method.

The principle of a voltammetric parallel multi channel measurement at microelectrode arrays is described in Electroanalysis 8, 10 (1996) 891. Strein and Ewing, Analytical Chemistry 65 (1993) 1203 suggest an electrode array having embedded carbon fibers of a diameter of 1 to 2 μm. Neither of said methods allows a serial electric inquiry of different sensor positions.

Yon Hin et al., Sensors and Actuators B1 (1990) 550 describe a multianalyte electrode array comprising meander-shaped parallel electrode strips for a parallel analysis of glucose and galactose by a conductivity measurement. For this purpose, glucose oxidase and galactosidase are polymerized in conductive polypyrrole on the electrode surfaces, controlled by an electropolymerization. Said array using the electric conductivity as a detection quantity, indexing processes have no importance with respect to voltammetric malfunctions.

A nano-structured gold electrode array for immunodetection is described by Musiel et al., Journal of Vacuum Science and Technology B13 (6)(1995) 2781. Said electrode array is stochastically distributed by extracting nano particles from an insulating layer applied on gold and cannot be individually addressed and read out.

U.S. Pat. No. 5,605,662 describes an electrode array comprising individually controllable individual electrodes of a diameter of substantially 30 μm and larger counter electrodes separated therefrom on a silicon chip. Said array is not used for electrochemical detection, but only for an addressing and field production between individual electrodes coated with gel and counter-electrodes positioned at the edge of said array. By said produced field, charged molecules are transported to individual electrode positions or removed from said fields by a counter-polarization. A concrete case, for which said method is described, is the concentration of DNA in a gel above individual electrodes for a DNA hybridization at catchers, and in a reverse case, the elimination of mismatches by a field support of the DNA stringency treatment, cf. Sosnowski et al., Proc. Natl. Acad. Sci., USA, 94 (1997) 1119. The use of said system for molecular biological multianalyte diagnostic is described in U.S. Pat. No. 5,5632,957, the electric transport being combined with an optical detection.

An array for a potentiometric application, said array having more than thousand individually addressable electrode elements, is described by Hermes et al., Sensors and Actuators B 21(1994) 33. The individual positions of said sensor array are actively switched on only at the time of readout, whereas, in the non-readout state, no potential is supplied and no reaction takes place. CMOS switches for switching the electrodes on and off are individually arranged at each array position. A similarly structured multi electrode array comprising nMOS switches at each sensor position has been described by Fiaccabriono et al. in Sensors and Actuators B, 18–19 (1994) 675. In this type of arrays considerable charging currents are generated considerably affecting amperometric detection methods. In Anal. Chem. 66 (1994) 418, Kounaves et al. describe an array having 19 iridium electrodes of a diameter of 10 µm as individually addressable electrodes. Said electrodes were read out serially by a 2-electrode technology, and supplied with a potential only in the readout state.

A survey of electrochemistry at ultramicroelectrodes is to be found in Physical Electrochemistry, Ed. Rubinstein, Marcel Dekker, 1995 New York, pp. 131–208.

The application of a pair of 20–300 nm structured interdigital electrode arrays for a marker-free impedance analysis of a molecule conjugation on the electrode surfaces has been described in DE-A 196 10 115 (as above). An individual pair of nano-structured interdigital electrodes for admittance spectroscopy of dissolved molecules has been described in J. Vac. Sci. Technol. A 13 (3) (1995) 1755. A similar principle of impedance measurement in an electrode interspace of immobilized molecules by an interdigital pair of nanometer electrodes evaporated on a pit wall is shown in PCT/EP 96/05290. In all described impedance measurements using ultramicroelectrodes, an interdigital electrode pair was connected to a commercial impedance measuring device by two-pole technology.

A particular type of individually addressable sub-µm strip electrode arrays has been described by Nagale and Fritsch in Analytical Chemistry 70, 14 (1998) 2902 as stacked thin-film electrodes insulated with respect to each other. The cross-sections of the stacks have been used as active electrodes. A commercial computer-supported potentiostat comprising a working electrode, a reference electrode and a counter-electrode, has been used for electrochemical control. The 15 electrode layers have been read out serially by switching on and off.

A microelectrode array for extracellular activity measurement and stimulation of living cells and neuronal tissues uses individually addressable microelectrodes having a diameter of 14 µm, said microelectrodes being applied by a CMOS VLSI chip for stimulation and detection, each chip electrode being adapted to individually record cellularly generated biopotentials between 0.9–2.1 mV and 100–400 µV, cf. Pancrazio, et al. Biosensors & Bioelectronics 13(1998) 971. For said stimulation, frequencies between 0.7 and 50 kHz with bias potentials of 12–16 µV are applied. The electrodes are operated serially in a switched-on or switched-off state.

A method and an arrangement for enriching and cleaning molecules at large-area electrodes is described in PCT/DE 97/01368. According thereto, only small field strengths are generated and no detection methods are included.

A modification and coating of surfaces with biomolecules, such as they are used for the electric sensor array, is achieved by a covalent binding or adhesion to the metallic or non-metallic surfaces or to the walls of compartments. The molecules are applied as monolayers or multilayers by a covalent binding, by adsorption, by inclusion in polymers or as adhesive films, cf. Mandenius et al., Methods in Enzymology 137 (1988) 388. An adhesive layer production over cross-linked layers applied in gaseous or liquid phase, cf. Williams et al., Biosensors & Bioelectronics 9 (1994) 159, on surfaces with functionalized silanes as monolayers, cf. Fischer et al., Europhysics Letters 28 (2) (1994) 129–134, is widely known. To said silane derivatives, which may carry amino, thiol, aldehyde, hydroxyl, carboxyl or other functional groups, a very wide range of other compounds having suitable reactive groups are covalently bound by cross-linking methods, cf. Bäumert/Fasold, Methods in Enzymology, vol. 172, p. 584. In this manner, all bioactive substances suitable as affinity-binding catcher molecules, such as oligonucleotides, peptides, haptens and others are to be immobilized on the electrode surfaces.

A specific immobilization making use of the metal surface is the formation of self-assembling monolayers by thiol/gold bonds. After the formation of a self-assembling monolayer, an ordered binding of proteins, such as antibodies, is obtained e.g. over streptavidin/biotin couplings, cf. Spinke et al., Langmuir 9 (1993) 1821. In another preparation, histidine-marked proteins are orderly linked to the surfaces on gold surfaces via thioalkane chelating agents, cf. Krödger et al., Biosensors and Bioelectronics 14 (1999) 155.

A further method for selectively applying organic adhesive and coupling layers is the electropolymerization, for example for linking ferrocenes on platinum electrodes, cf. Karnau et al. in Anal. Chem. 66(1994) 994.

A number of methods for producing biomolecular arrays in microdimensions are customary. Putting miniaturized rings onto chip surfaces is derived from macroscopic stippling, said surfaces having been coated by immersion with corresponding molecules in advance, cf. [Rose, J. Ass. Lab. Autom. 3, 3 (1998) 53].

Blanchard in Genetic Engineering, Principles and Methods, 20 (1998) 111 succeeded in providing a piezoelectric printing method, similar to ink-jet printers, for structuring DNA-Chips.

The so-called micro contact printing, i.e. the transfer of molecules by microstamps has been described by Kumar and Whitesides, Appl. Phys. Lett. 63 (1993) 2002.

Mcgall et al., Proc. Natl. Acad. Sci., USA 93 (1996) 13555 suggested a solid phase synthesis on chip microareas, said synthesis permitting a nucleotide constitution by photoactivation.

According to U.S. Pat. No. 5,605,662, charged molecules are transported by electrochemical focusing from the solution to their binding positions in gels over electrodes.

Due to perforated membranes which are pressed onto chip surfaces, immobilization reactions at the open positions are possible on the surfaces in the liquid phase, cf. Ermantraut et al., Proc. of µTAS'98, Alberta, Can., 1998, p. 217.

The mentioned methods represent standard methods permitting an immobilization of DNA, oligonucleotides, proteins and other molecules at array positions.

SUMMARY OF THE INVENTION

A disadvantage of all electric sensor array arrangements having been described so far and comprising electrodes as transducers, is that they are only suited for mono analyte determination, or that the actual sensoric function has to be taken over by additional optical components. The electrode systems so far called "arrays", e.g. interdigital electrodes, do not represent arrays in a proper sense, adapted for a multi analyte measurement. Moreover, prior described electrode arrays could not be read out by serial methods usual in computer technology, i.e. subsequently, without disturbing the electric double layer which is formed by polarization at the electrodes in voltammetric detection methods.

Consequently, an array arrangement for a multi analyte measurement is desirable, improving said situation, and providing a purely electric sensor function by being adapted to be carried out by electric control and measuring methods.

It is an aspect of the invention to provide a sensor array for biochemical affinity assays, which array may be produced by semiconductor technology methods and which, as an electrochemical transducer, produces electric signals that are simple from a measurement technical point of view and that are directly selectable with regard to their position, without requiring optical components.

According to a further aspect, a measuring method is provided. Different analytes are simultaneously determined from mixtures of substances.

In a further aspect, a method for serially electrically reading out said sensor array is provided, said method avoiding interferences in the electric measuring process and being compatible with computer technological methods.

Miniaturization, production and handling advantages are further aspects.

Improved analytical handling of molecular biological assays is an even further aspect of the invention.

The invention refers to using a plurality of ultramicroelectrodes, i.e. preferably electrodes having typical structural dimensions of below 1 µm, as sensor element and to positioning them as arrays on a carrier. Besides a miniaturization, the arrangement of the ultramicroelectrodes in a corresponding array is intended to provide an advantageous diffusion behavior of the molecules to be detected and further to a use of voltammetric and impedimetric detection methods, such as redox recycling and marker-free impedance measurements, for which methods electrodes of this type are indispensable.

Further, the invention relates to a specific serial addressing method (for reading out and transporting) of the electrochemical processes at the sensor positions (arrays). The ultramicroelectrode arrangement according to the invention equally refers to the production of multiple electric fields having very high field strengths, said fields being adapted for actively transporting molecules individually at all sensor positions.

The invention provides an electric sensor array for a multi analyte measurement of biochemical molecular assays, said sensor array comprising the following:

(a) a mechanically stable planar substrate, on which several sensor positions are provided as an array, each sensor position comprising locally separated ultramicroelectrodes at least present in pairs, and optionally additional auxiliary electrodes, (b) insulated wirings allowing each sensor position and each individual electrode to be individually electrically addressed, (c) additional electric wirings allowing an electrochemical control and regulation at each position, and optionally electric direct and/or alternating fields at each sensor position, (d) an immobilization of different or identical affinity-binding molecules which are bound directly or to particular carriers or gel-like substances on all or on selected surfaces of the individual sensor positions or included therein, and which are arranged individually above the individual sensor positions, (e) integrated electronic functional elements, providing an individual control of electrochemical reactions at the individual sensor positions and independently thereof an individual electric measurement of said reactions at each position, the electronic control elements being attributed to groups, lines or individual positions of said sensor arrays.

The invention provides a serial, i.e. subsequent, electric readout of the electrochemical processes at individual sensor positions by active control elements, preferably in the substrate. The active switch, control and readout functions at each sensor position are effected such that an electric double layer, which is formed at the microelectrodes in electrochemical processes, is not disturbed.

Intelligent electronic functional elements provided as separate components or directly at the individual sensor positions further permit electrochemical processes to be recorded for a readout at a sensor position in time intervals between the addressing procedures, and thus to be temporarily stored.

The invention provides an electric sensor array adapted to resolve different analytic problems by a variable number of specific sensor positions for different analytes. Further, the invention describes a method for effecting particle-tolerant measurements in sub-µl-volumes per sensor position with the electrodes used for detection, i.e. independently of optical properties.

It is advantageous to produce the sensor element using wafer-oriented technologies of the semiconductor industry which are also compatible with the methods for immobilizing or charging biochemical affinity-binding detector molecules at the array positions.

According to a particular embodiment of the invention, variability of the arrangements and methods is achieved.

A sensor array having less than about 50 electric sensor positions has ultramicroelectrodes that are connected to (uncovered) contact surfaces by direct paths below an insulating layer. For said application, silicon, glass, ceramic or polymers are advantageously used as planar substrates.

Both, small and large numbers of sensor positions per sensor array are realized by integrating the wiring using Si-chip-technology. Silicon is used as a planar carrier element particularly if individual sensor elements or positions are intended to be arranged as densely as possible.

Silicon is also used as a carrier for the sensor array, because it allows an efficient technology to be used and is particularly useful when additional electronic elements, such as transistors, diodes, resistances and other usual electronic components are integrated in the carrier relative to a position, for individually controlling the sensor positions of the sensor array, for controlling and switching as well as reading out the individual sensor positions.

Independent control and a serial electrochemical detection at the sensor positions is used for both, the electric sensor positions with direct contacting and those with integrated electronic elements at the individual sensor positions. For said electrochemical detection, electric double layers at the electrode surfaces obtained by electrode polarization are continuously applied to all sensor positions. This is embodied by changeover switches which avoid that said polarization be disturbed by serial electric readouts, i.e. successive readouts at time intervals, of the individual sensor positions, and no so-called charge reversal processes occur.

Simultaneously using the ultramicroelectrodes for detection, optionally supplemented by further auxiliary electrodes, as elements for effecting electrophoretic transportation processes of the analyte molecules to the positions of affinity-binding partner molecules and also for eliminating undesired binding events, is of particular advantage.

Interferences in polarization are avoided by an arrangement for electric control which continuously supplies the arrays which are no longer addressed with a polarization voltage. The continuous supply lasts until the subsequent addressing time at which an information of the sensor position is again inquired. Said electric control during non-addressing time intervals is adapted to provide a current supply, preferably by a substantially galvanic or ohmic connection from a corresponding array to a source supplying the potential, particularly far off the sensor position.

Three qualities of guided wiring are provided. One guided wiring serves for addressing, thus for selecting an array, a column or a line of arrays. A further guided wiring serves for transmitting signals (current, voltage, potential or such courses) with respect to a corresponding individual sensor position. A third guided wiring serves for supplying the described polarization voltage or such potentials, for supplying to the arrays which are not addressed (i.e. not read) at the moment.

Preferably, the guided wiring for reading out and for supplying the polarization voltage (conservation voltage) extend in parallel and coupled with the carrier. It is also preferred that the guided wiring for addressing extends perpendicularly with respect thereto.

With the exception of the "further wirings", said guided wiring may also be provided outside of the carrier.

The changeover or alternating switches change the attribution of the electrodes either to one or to the other guided wiring, depending on the addressing state. A state in which the connections of the electrodes are "not connected" (n. c.) does not exist. Controlled and interference-free changeovers from the measuring potential to the conservation potential and a temporary recording and storage of the events which may be detected by the addressing procedure are provided. The feature of a temporary recording is particularly advantageous, for not uselessly having to spend time between the non-addressed periods. Due to the electric control and the conservation potentials, the process may be continued without interruption and the time between two recordings may also be actively used.

Embodiments are exemplified using figures and corresponding description.

BRIEF INTRODUCTION TO THE FIGURES

Figure 3:
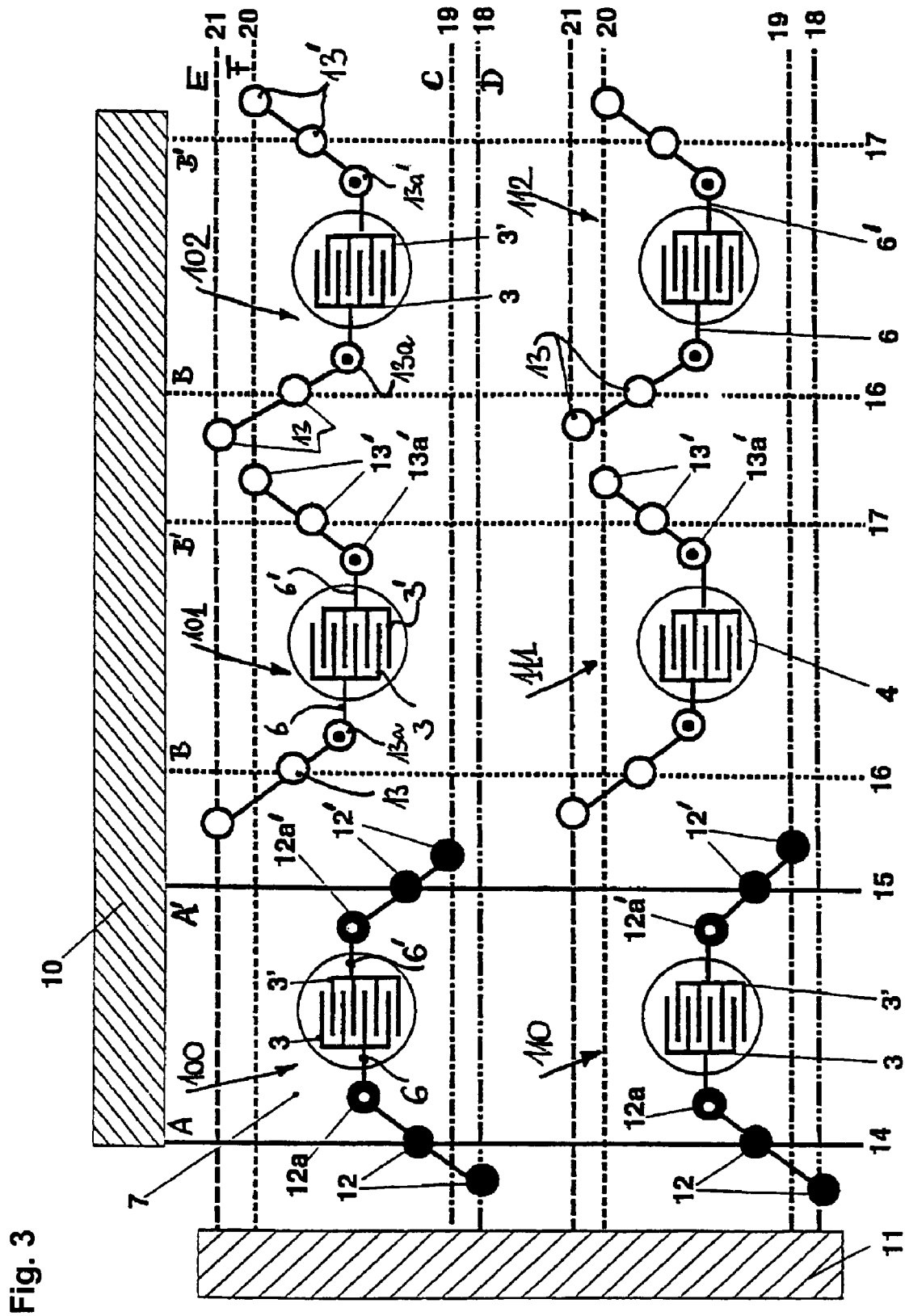
FIG. 3 is a schematic illustration of an array of pairs of interdigital ultramicroelectrodes having active CMOS switching elements for addressing and controlling the individual electrode polarization and external reading and measuring amplifiers.
Figure 3A:
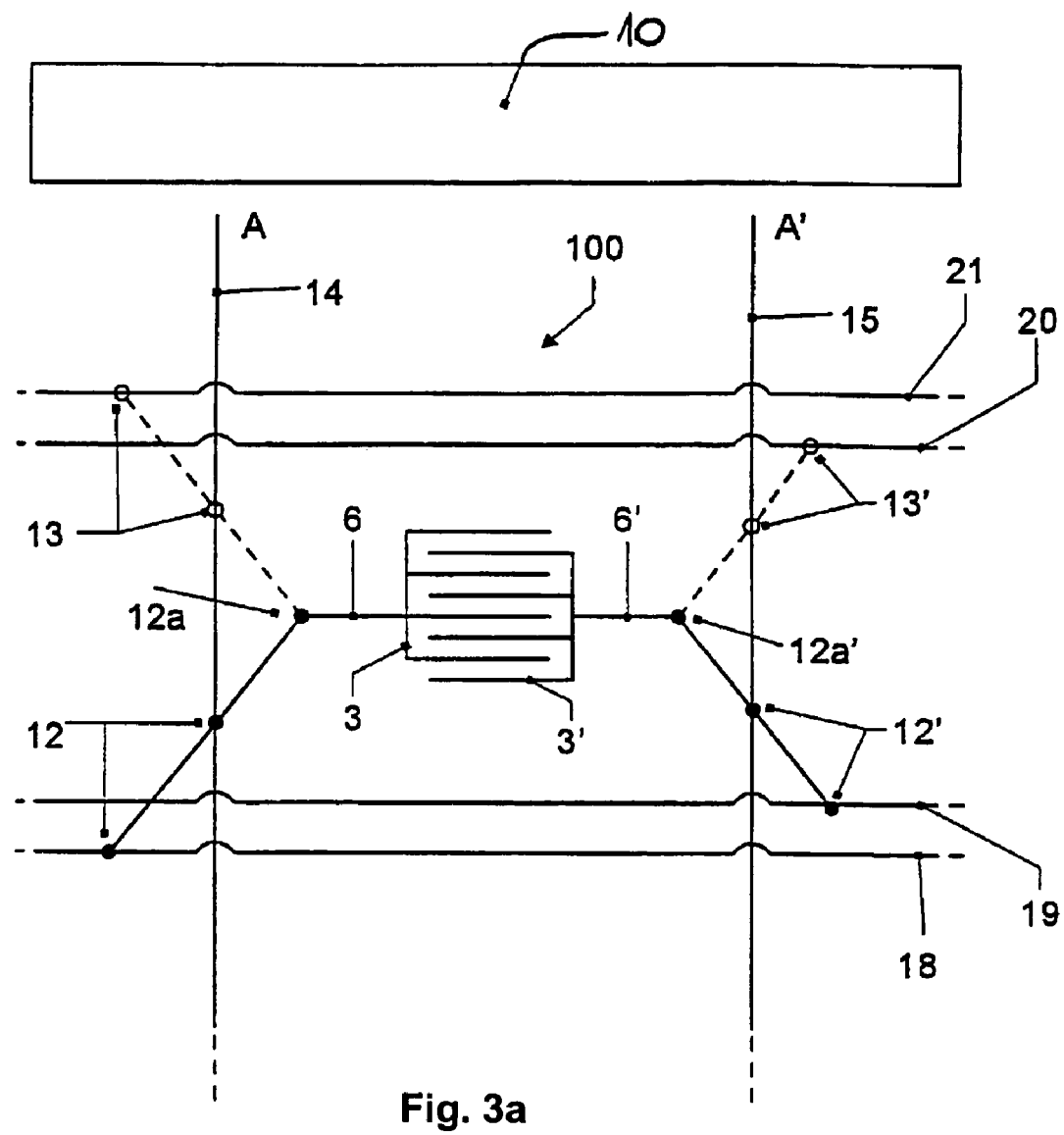
Figure 3B:
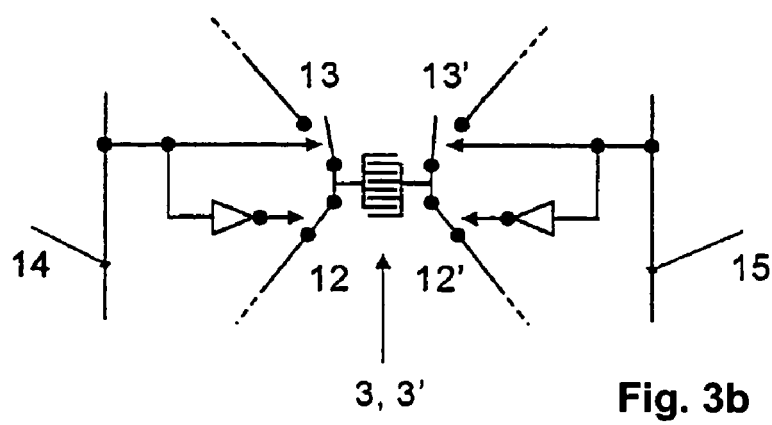

FIG. 3*a* is a selective enlargement of a sensor position from FIG. 3, showing all possible connection paths to the two ultramicroelectrodes, in this embodiment, however the connection path via a switch 12 (integrated circuit in an addressed state) being connected through. A connection path 13 marked by a broken line is not connected through, thus blocked.

Figure 4:
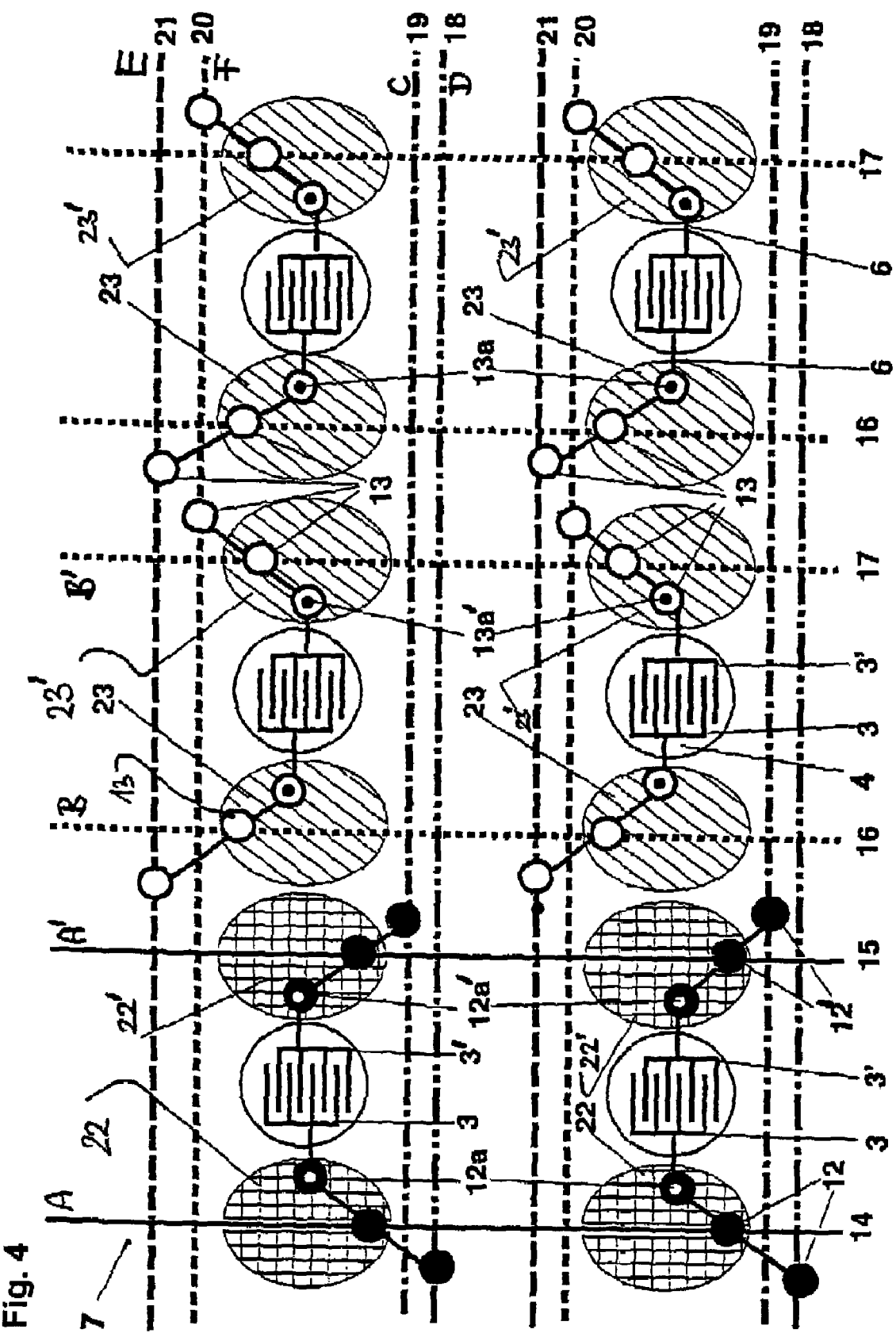

FIG. 4 is a schematic illustration of an array of pairs of interdigital ultramicroelectrodes having active CMOS switching elements for addressing and controlling the individual electrode polarization, said array comprising a control amplifier, reading and control means 22,23 at each sensor position as well as external reading and measuring amplifiers.

Figure 5:
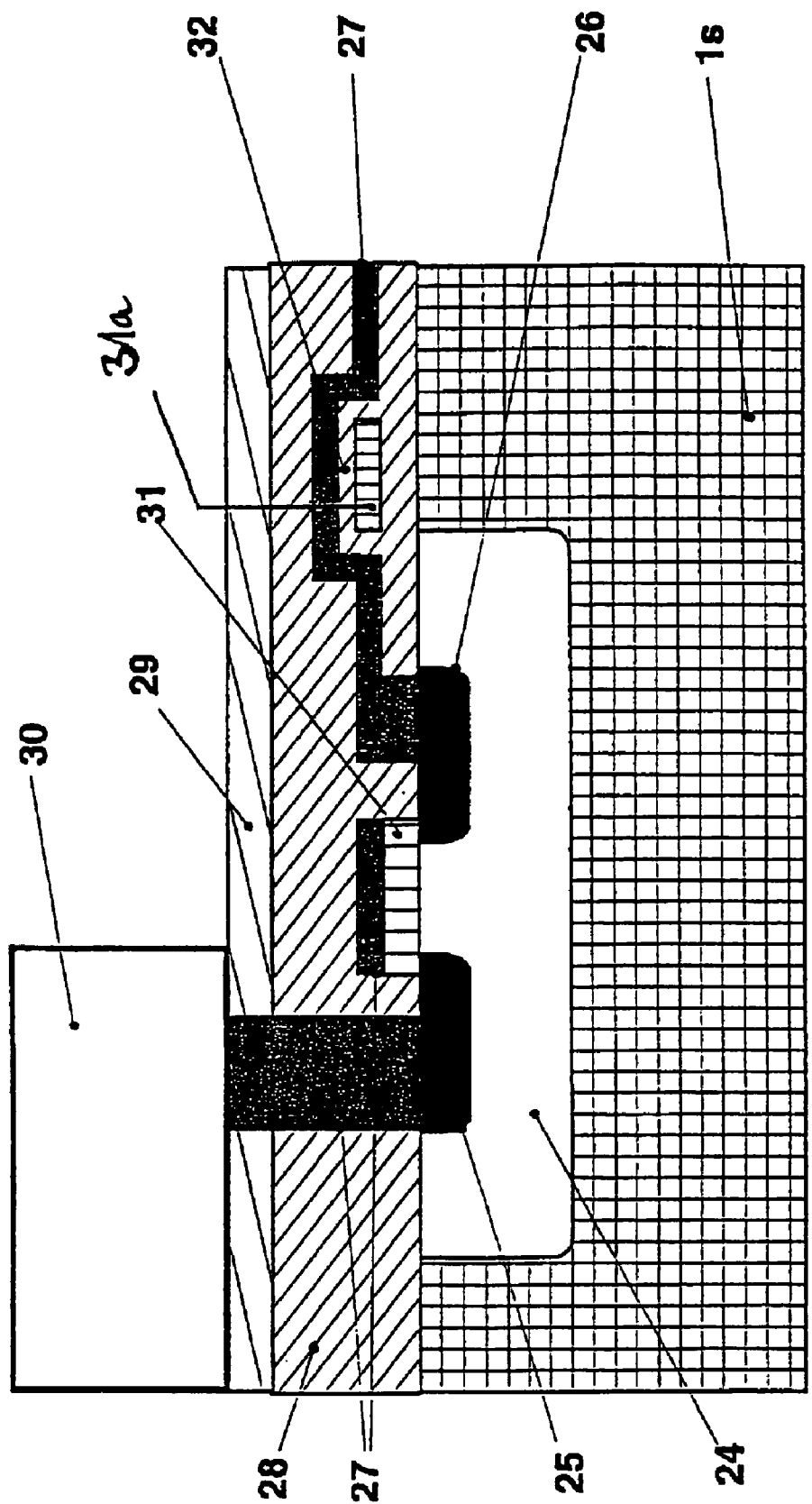

FIG. 5 is a schematic illustration of an arrangement of array electrodes and integrated CMOS elements.

Figure 6:
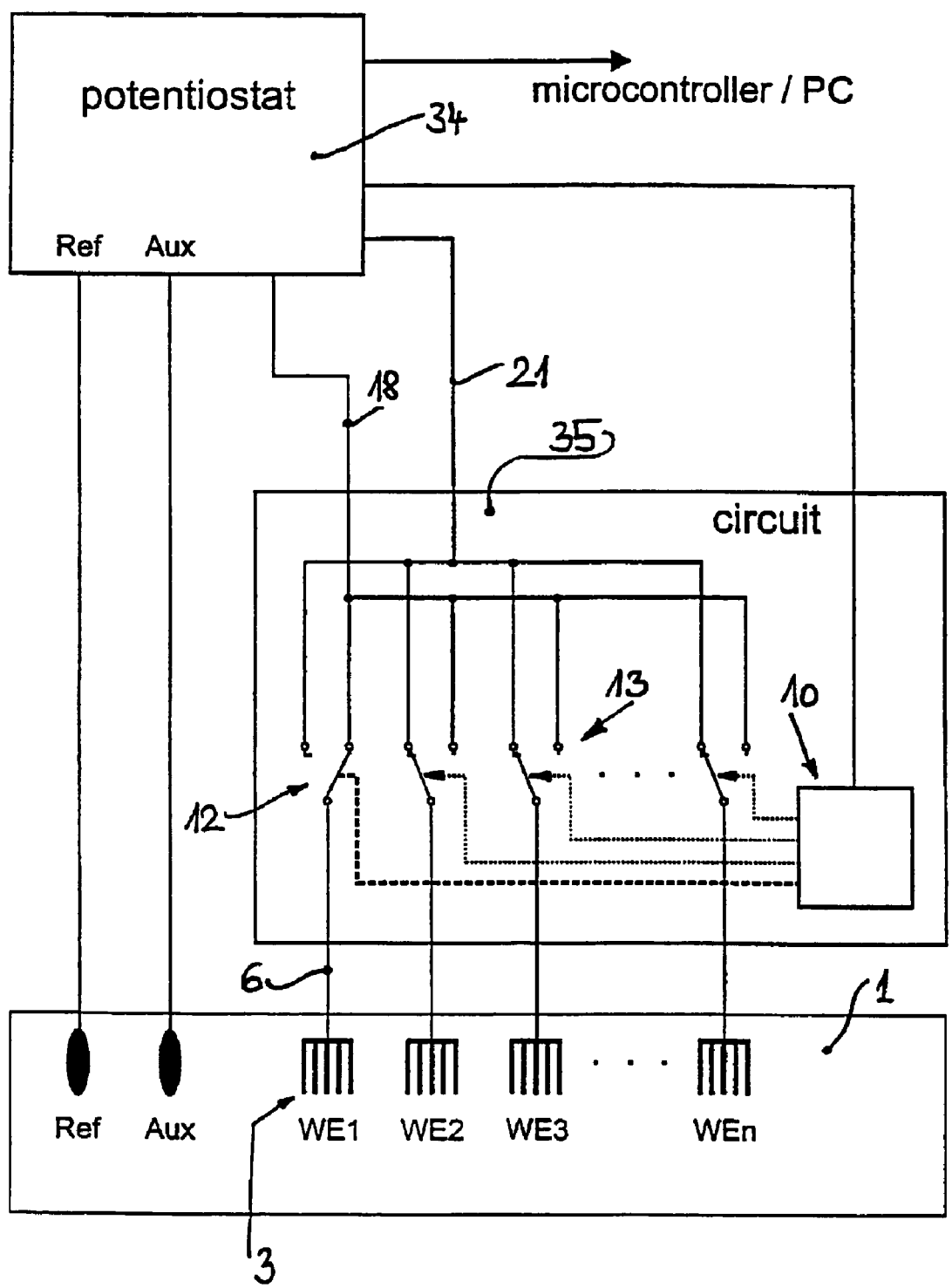

FIG. 6 illustrates the control of an electrode array according to FIG. 1, the switches 12 and 13 being schematically indicated, controlled over a multiplexer 10 (1 out of n-decoders). It is visible that those measuring cells (designated here as WE1, WE2, WE3) which are not activated for a readout are supplied to an equilibrium potential together with the switch elements 13 which can be structured in the same manner as indicated in FIGS. 3, 4 and 5. The switch element WE1 is illustrated in a currently addressed state, by a switching state 12, corresponding to a circuit 12 of FIG. 3 and its connection path.

Figure 7:
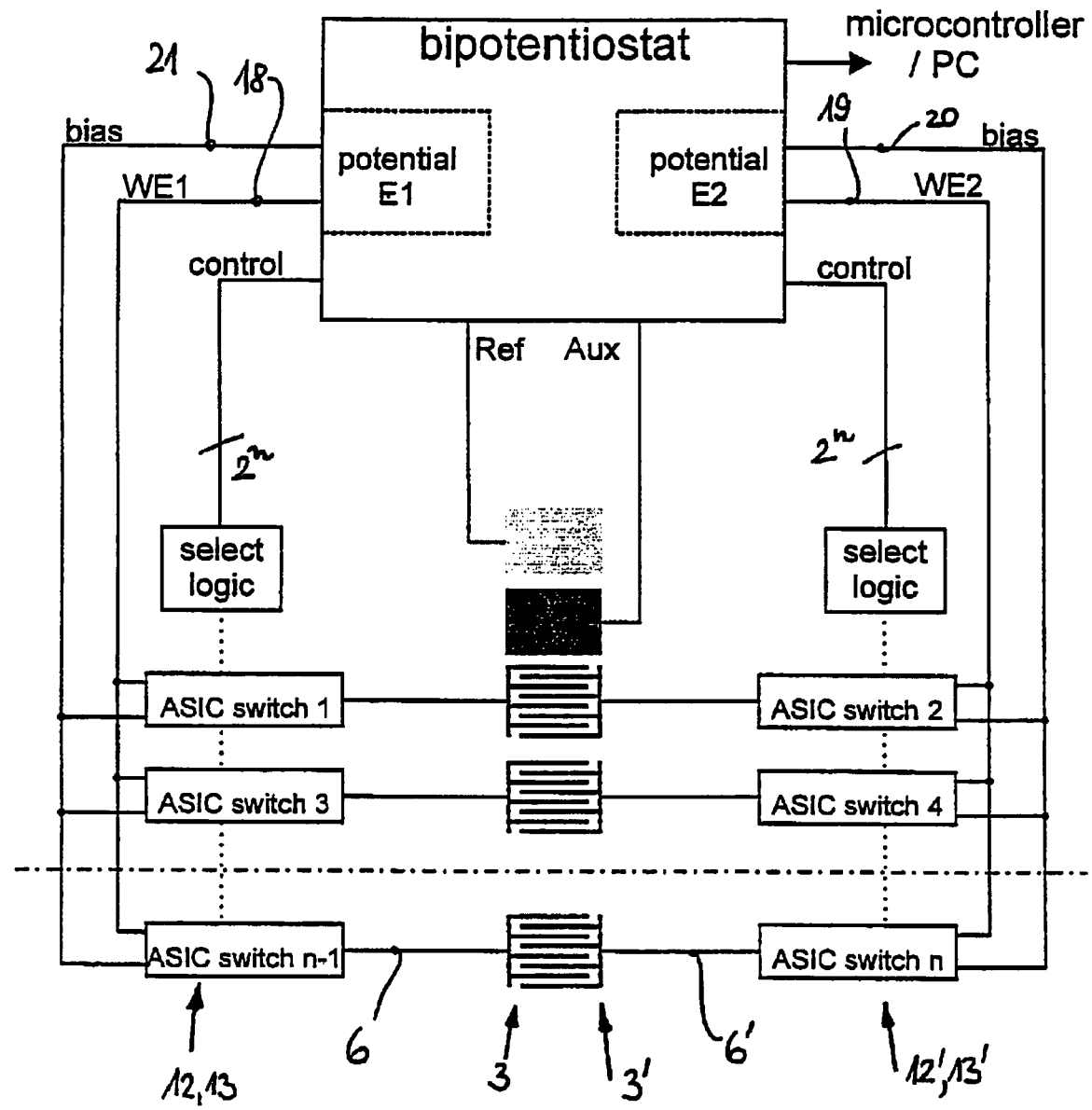

FIG. 7 shows a voltammetric measuring circuit comprising electrode arrays for a redox recycling according to an embodiment of use 10 which will be described further below, for controlling the array according to FIG. 1 or FIG. 3.

Figure 8:
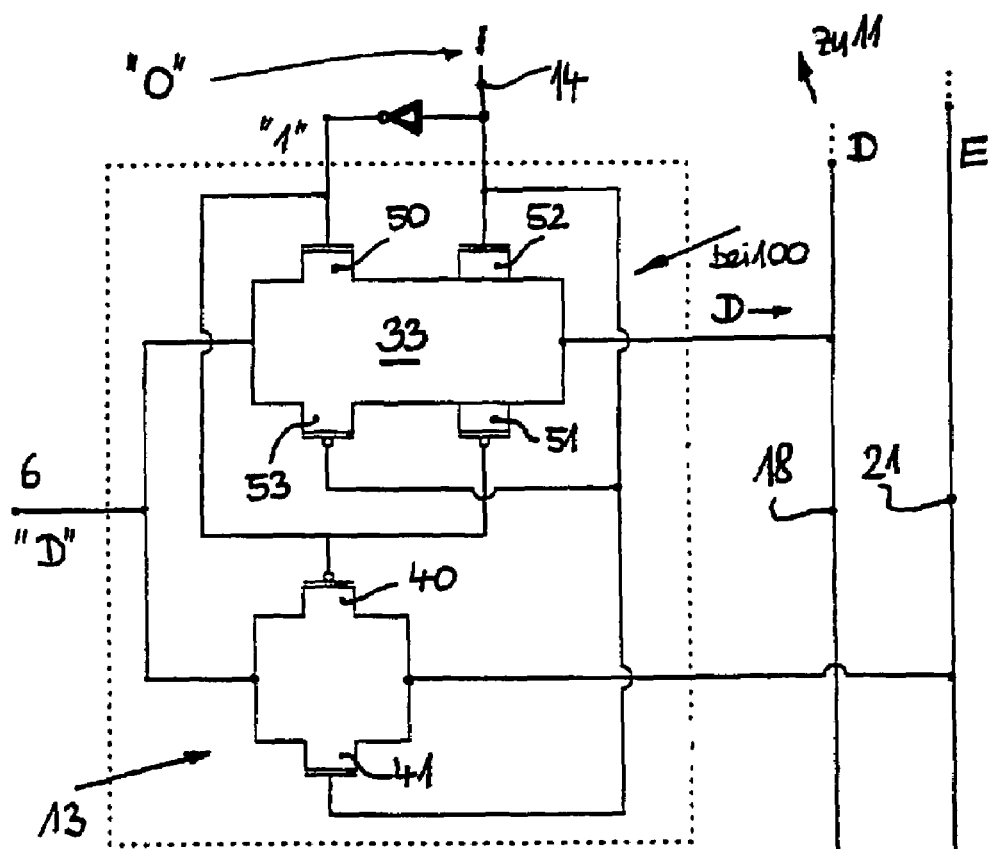
Figure 8:
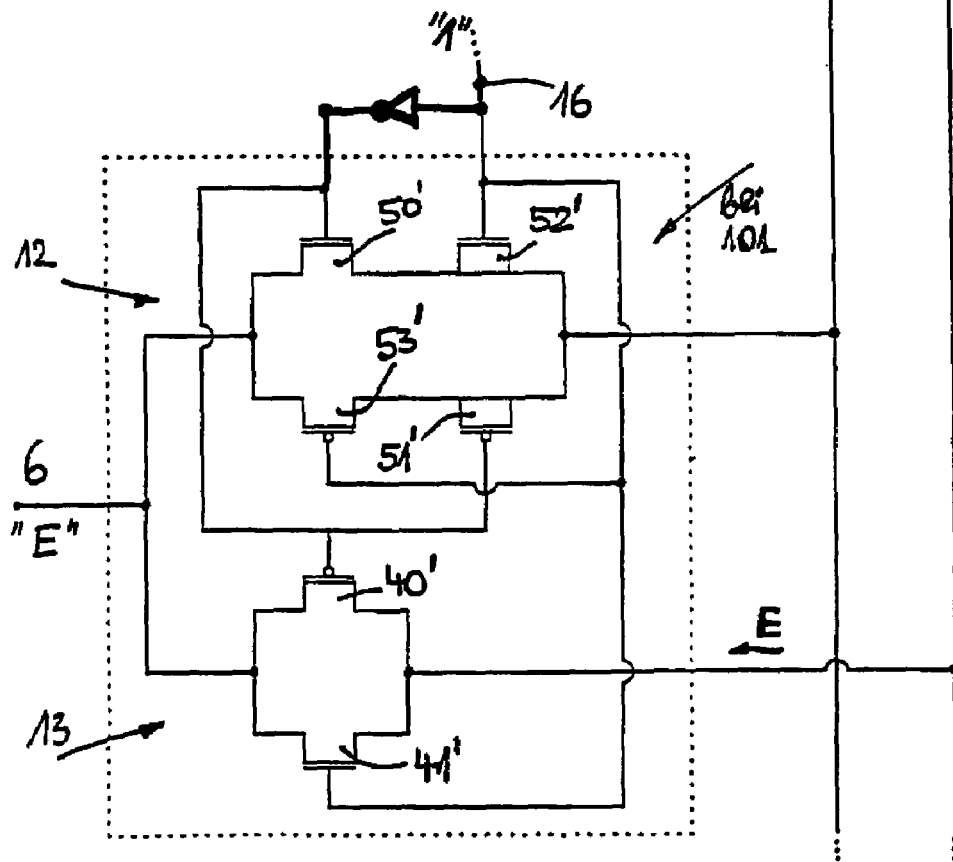

FIG. 8 shows the integrated circuits 12, 13 of FIGS. 3 and 4 in a schematic illustration comprising several CMOS switches which are controllable over addressing lines 14.

Figure 8A:
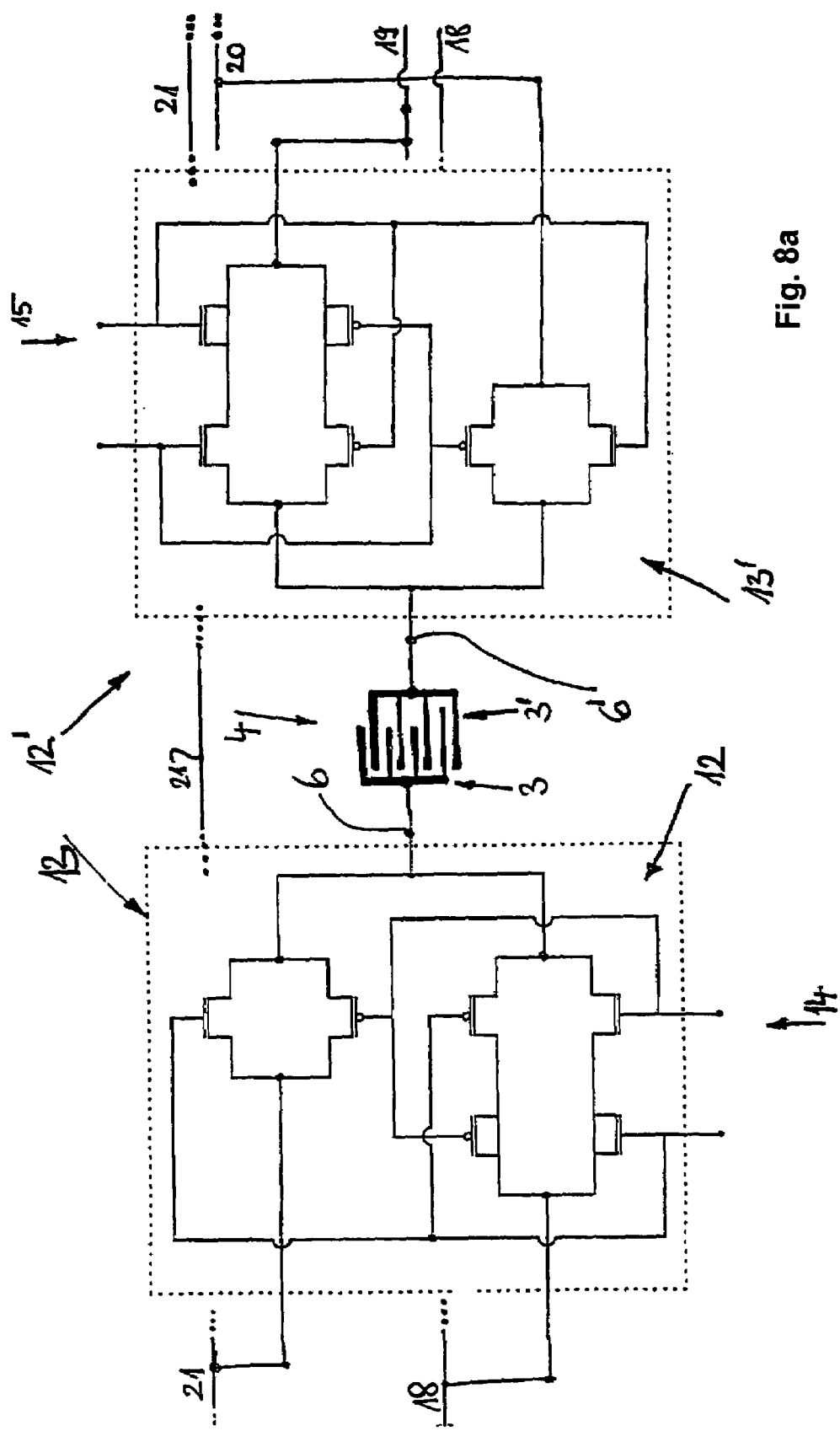

FIG. 8*a* illustrates the embodiment of FIG. 3, shown in detail in FIG. 3*a*, comprising CMOS switches (as transmission gates) according to FIG. 8.

Figure 9:
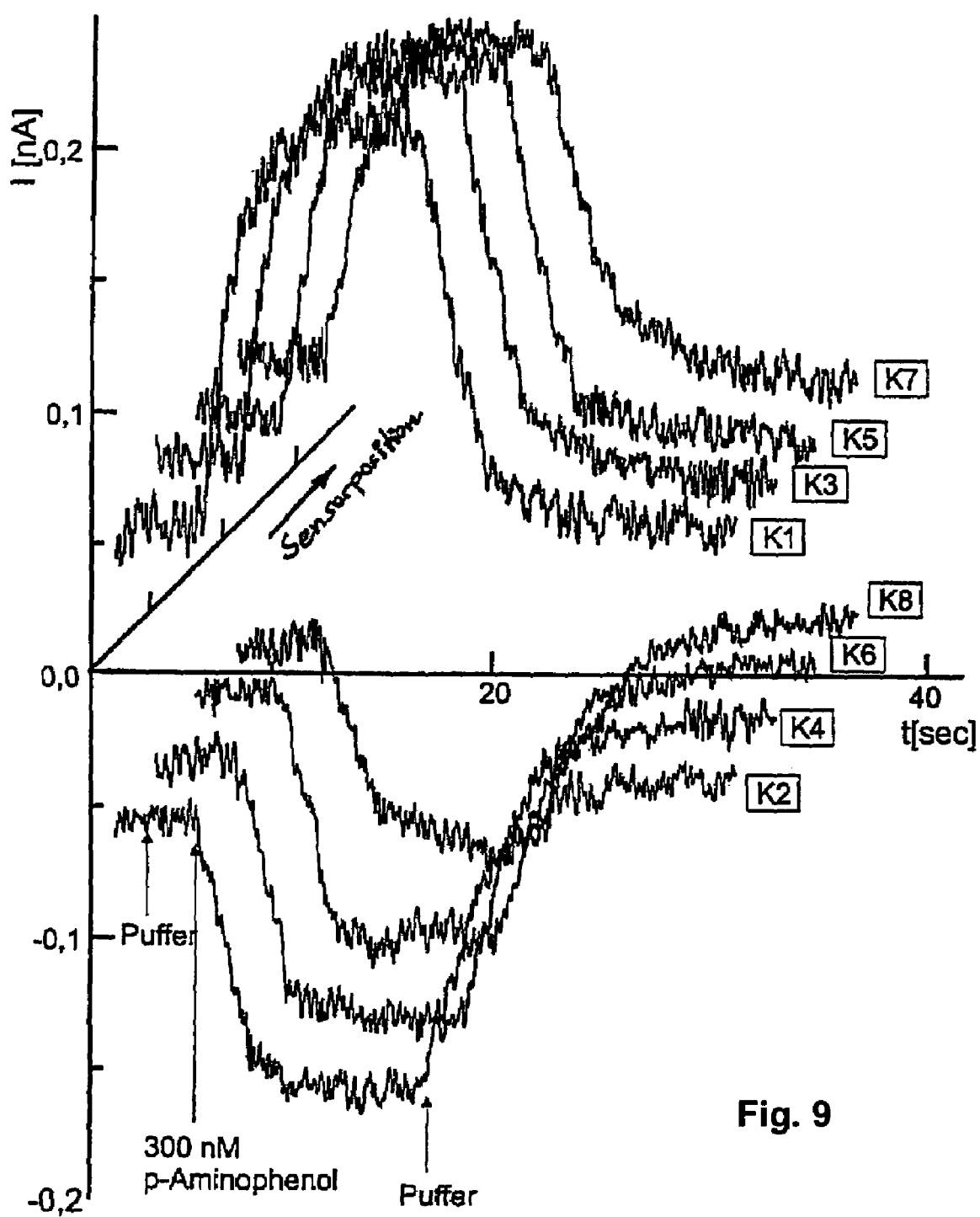

FIG. 9 shows a measurement diagram of the electrochemical redox recycling of p-hydroxyaniline, which diagram is obtained according to embodiment 16. Each of the indicated long-time curves K1 to K8 comprises several measuring points, which in the illustration are interpolated and superimposed by a measuring random noise. The measuring time per point is between 20 msec and 100 msec.

DETAILED DESCRIPTION OF THE EMBODIMENTS

| | Some reference numerals in the figures. |
|---|---|
| 1 | planar carrier |
| 1s | silicon substrate |
| 2 | contact surfaces |
| 3a | annular ultramicroelectrode system |
| 3a' | annular ultramicroelectrode system |
| 3b | auxiliary electrode |
| 3c | auxiliary electrode |
| 3, 3' | pair of interdigital ultramicroelectrodes |
| 3d, 3d' | pair of interdigital electrodes |
| 3e, 3e' | pair of auxiliary electrodes |
| 3f, 3f' | ultramicroelectrode array |
| 3g, 3g' | pair of interdigital electrodes with ultramicroelectrode array |
| 3h, 3h' | pair of electrodes with ultramicroelectrode arrays |
| 3i, 3i' | meander-shaped ultramicroelectrodes |
| 3j | auxiliary electrode |
| 4 | areas of sensor positions |
| 5 | cover of electrode supply lines and control lines (paths) |
| 6, 6' | metallic paths to the electrodes 3,3' |
| 6" | metallic paths to the auxiliary electrodes |
| 7 | silicon dioxide |
| 8 | compartment material |
| 9 | dot-shaped ultramicroelectrodes |
| 10 | electronic addressing and decoding means |
| 11 | electronic means having reading amplifiers |
| 12, 12' | integrated circuit in addressed state |
| 12a, 12a' | through-contacting |
| 13, 13' | integrated circuit in non-addressed state |
| 13a, 13a' | through-contacting |
| 14 | active addressing line A |
| 15 | active addressing line A' |
| 16 | inactive addressing lines B |
| 17 | inactive addressin lines B' |
| 18 | measuring line signal C |
| 19 | measuring line signal D |
| 20 | bias line signal E |
| 21 | bias line signal F |
| 22, 22' | addressed integrated reading, amplifying and storing electronic |

-continued

Some reference numerals in the figures.

| | |
|---|---|
| 23, 23' | non-addressed integrated reading, amplifying and storing electronic |
| 24 | CMOS well |
| 25 | source |
| 26 | drain |
| 27 | CMOS aluminum |
| 28 | CMOS dielectric |
| 29 | liquid-resistant passivation |
| 30 | gold electrode |
| 31 | polysilicon gate |
| 31a | polysilicon line |
| 32 | crossing of addressing line and measuring line |
| 33 | capacity compensated switch (FIG. 8) |

Figure 1A:
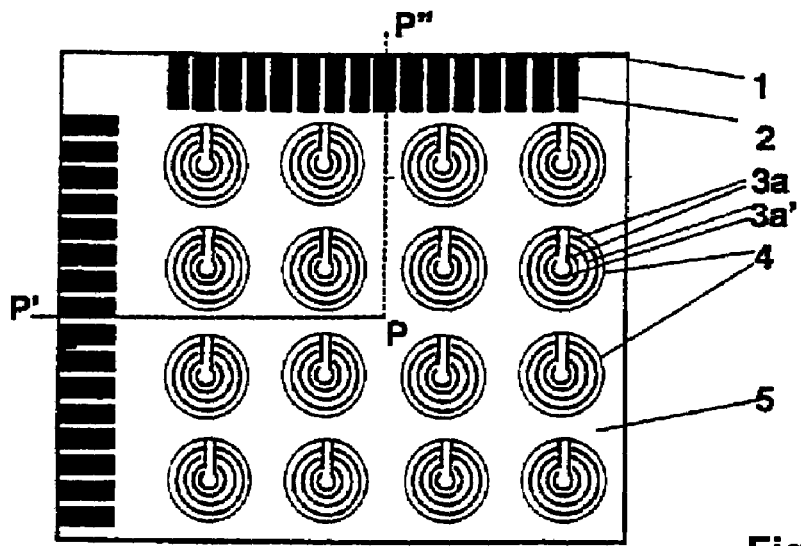
FIG. 1 show an array of interdigital ultramicroelectrodes comprising pairs of microelectrodes and details of individual sensor positions.
Figure 1B:
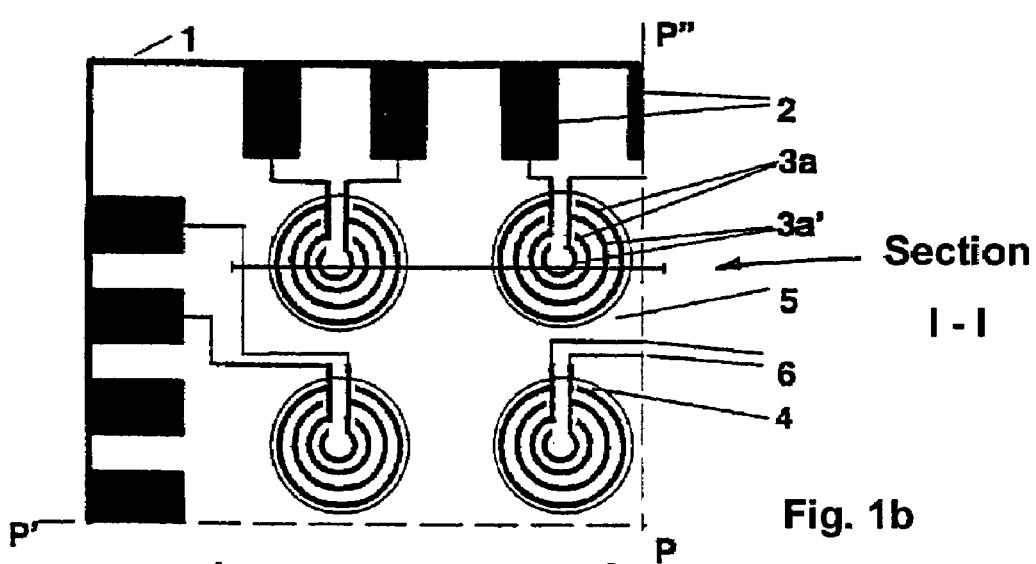
Figure 1C:
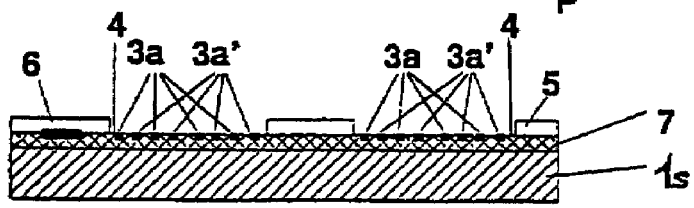
Figure 1D:
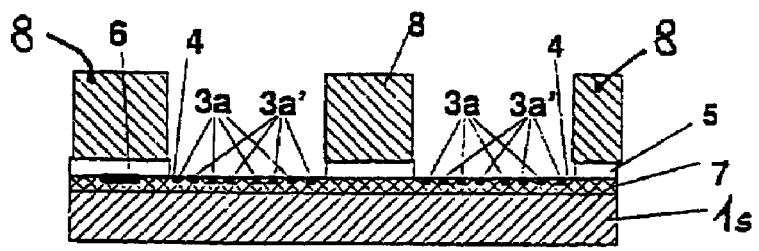

In FIG. 1a, a silicon chip is shown with one pair of ring-shaped microelectrodes 3a and 3a' each being arranged at each array position 4 (sensor position), said microelectrodes extending through direct paths to electric connecting contact surfaces 2 at the edge of the chip. In FIG. 1b a selective enlargement of a detail of the chip of the array element according to FIG. 1a is shown in section PP'. Annular electrodes 3a and 3a' are conducted from each array position 4 to an individual contact surface 2 at an edge of the chip through paths 6. Said paths 6 are covered by a liquid-sealed insulating layer 5. A cross-section of said illustration along a sectional line I—I is shown in FIGS. 1c and 1d. An insulating layer of silicon dioxide 2 is applied onto a silicon substrate 1, said insulating layer carrying the electrodes 3a and 3a' as well as the paths 6 as thin-film metal structures. The paths 6 are covered by the insulating cover layer 5, whereas the active electrodes 3a and 3a' remain uncovered in said array positions 4. Said cover layer 5 also serves as a delimitation between the electrodes of the individual array positions. In FIG. 1d, said cross section I—I is illustrated, comprising an additional thicker polymer layer 8, serving for providing microcompartments (compartments) or distance rings at the array positions comprising the ring electrodes 3a and 3a'.

In FIG. 2, individual array positions 4 comprising different arrangements of ultramicroelectrodes and auxiliary electrodes are illustrated. FIG. 2a is a detailed illustration of a pair of annular ultramicroelectrodes 3a and 3a' comprising connecting paths 6 at an array position 4 according to FIG. 1a. In FIG. 2b, annular strip electrodes 3a and 3a' as well as 3c are arranged, and additionally a central circular auxiliary electrode 3b in the center of said strip electrodes. FIG. 2c is a detailed illustration of a pair of ultramicroelectrodes 3 and 3' comprising discharge paths 6, 6' at the array position. FIG. 2d shows 2 pairs of interdigital ultramicroelectrodes of a different geometry comprising narrow electrode structures 3 and 3' and enlarged structures 3d and 3d' with individual connecting paths 6. In FIG. 2e, an interdigital ultramicroelectrode pair 3 and 3' is arranged with two metallic auxiliary electrodes 3e and 3e'; the connecting paths of said auxiliary electrodes are designated 6". FIG. 2f shows a pair of interdigital ultramicroelectrodes 3 and 3' and two two-dimensional auxiliary electrodes 3f and 3f' covered by an insulating layer 5. In said cover layer 5, active electrode surfaces 9 are uncovered in a dot-shape, said electrode surfaces being connected in parallel. In FIG. 2g, a pair of interdigital electrodes 3g and 3g' having a similar structure as said auxiliary electrodes 3f and 3f' is shown. Said dot-shaped electrodes 9 are electrically connected with each other according to a finger structure. FIG. 2h illustrates a pair of two-dimensional electrodes 3h and 3h' which are also covered by a cover layer 5 and comprise dot-shaped electrodes 9. In FIG. 2i, a meander-shaped electrode pair 3i and 3i' is combined with a planar (W-shaped) auxiliary electrode 3j.

To simplify matters, the above illustrations in all FIG. 2 (FIG. 2a to FIG. 2i) are functionally numbered. Connecting paths, leading to the main electrodes 3, 3' are designated 6, 6', independently of the specific geometrical structure of the main electrodes. The connecting paths to the auxiliary electrodes are designated 6", also independently of the specific geometry and design of the auxiliary electrodes. The following description is based on main electrodes 3, 3', and the connecting paths are also functionally numbered 6, 6', even if different connecting paths are present at different array positions. From a functional point of view, practically all array positions of a plurality of identically designed array positions (sensor positions) are identical, only being differently arranged on the substrate 1, so that designating functionally identical elements by identical reference numerals throughout the complete specification is considered to be helpful for a general comprehension. The same is valid for the CMOS switches 12, 13 explained further below, which are designated by their switching state.

FIG. 3 illustrates an array comprising pairs of interdigital ultramicroelectrodes 3, 3', in which the addressing and control of the electrode polarization by CMOS switches 12,12' and 13, 13' in the silicon chip 1 are arranged at each individual interdigital system 3 and 3' (sensor position 4). A liquid-sealed cover 7 is positioned above said switch plane. The paths 6,6' in the plane of the ultramicroelectrodes lead through openings at positions 12a, 12a' and 13a, 13a' in said insulating cover layer 7 (FIG. 1) to the plane of the CMOS switches situated further below.

Addressing lines 14 and 15, 16 and 17 are controlled by an electronic addressing unit 10 provided on the silicon chip.

The switches 12, 12' show an activated switching state, reading out a column of ultramicroelectrode pairs. The addressed ultramicroelectrodes are connected with measuring lines 18,19. Said lines 18, 19 lead to a reading amplifier 11. Switches 13, 13' are in a neutral position, the non-addressed ultramicroelectrodes are connected with bias lines 20, 21.

Signals are supplied to the above described measuring lines, bias lines and addressing lines, said signals being active at different times. Addressing signals A, A' are an activating signal for the left (vertical) column of the sensor positions 4, here sensor positions 100 and 110. The addressing signal A activates the switch 12 which couples the electrode 3 to the measuring line 18 over a path 6 and a through-contacting 12a. The addressing signal A' activates the switch 12' which connects the opposite electrode 3' to the second measuring line 19 via the opposite path 6', the opposite through-contacting 12a'. A measuring signal C,D is generated at the measuring lines 18, 19, which measuring signal may be received, stored and/or evaluated by a measuring amplifier 11. The non-activated columns of the sensor positions 101,111 and 102,112, which are shown in the middle and on the right of FIG. 3, operate in the same manner. As an example, the center upper sensor position 101 shall be described, in which an addressing signal B switches on a switch 13 such that an electrode 3 is connected to a bias potential E of a line 21 via a path 6, a through-contacting 13a. The switch 12 leading to said through-contacting 13a is deactivated, so that no measuring signals are received from said array position which is in a deactivated state. On the opposite side, at the electrode 3' which is connected to a bias line 20 with a potential F via a path 6', a through-contacting 13a' and a switch 13', the same happens. Here, the corresponding switch 12' is also deactivated. Thus, the non-addressed sensor positions are connected with the bias lines 20, 21 via the switches 13, 13', so that the electrodes 3, 3' are not left to an optional potential, but to a potential predetermined from outside.

With respect to FIG. 3 and also to FIG. 4, which will be described further below, the following has to be considered. For illustrating the switched-on state for measuring (lines 18, 19 with signal potentials C, D) and the "switched-off states" (bias lines 20, 21 with signals E, F), each sensor position 4 is marked only such that its current switching state of the switches 12, 12' and 13, 13' is illustrated. On the entire chip, each sensor position is, however, designed like a superimposed version of the left upper and central upper sensor array, thus comprising two switches 12, 12' for connecting one individual sensor position 4 to the measuring line 18, 19 and two switches 13, 13' for connecting the same through-contactings 12a, 12a' to the bias lines 20, 21, when the lower switches 12, 12' are neutral. Only one of said switch pairs is active, such as marked in FIG. 3 for different sensor positions 4. In other words, the interdigital electrodes 3, 3' are connected to the measuring lines 18, 19 with the two lower switches 12, 12', several of said measuring lines extending in parallel at a distance with respect to each other, for each line of interdigital electrodes. The switches 12 and the switches 12' are switched on in a vertical line over the addressing lines 14, 15 and the addressing signals A, A'. Simultaneously, the addressing lines B, B' for the other interdigital columns are also present, they only have another switching state, so that the switches 13, 13' belonging to the same interdigital electrodes that have just been described, are switched on. In case of a change, thus when switching off the switches 12, 12' leading to the measurement, the switches 13, 13' which lead to the bias line 20, 21 switch on and provide a controlled and interference-free changeover from the measuring potential to a conservation potential. As long as the conservation potential of said line 20, 21 is supplied to the electrode pairs 3, 3', and these are all electrode pairs which are not positioned in a vertical column addressed at the moment, polarization is not disturbed and no charge reversal processes occur. Thus an intermediate recording during the non-readout (addressed for being read out) state is permitted, so that during the non-readout state, no time is wasted which does not serve for recording a signal. In fact, the signal is also recorded here and stored in circuits 23, 23' described according to FIG. 4 to be read out later in a subsequent addressing process.

In FIG. 4, a sensor array is shown comprising pairs of interdigital ultramicroelectrodes, said array corresponding to the arrangement of FIG. 3. The ovally rimmed portions 22, 22' and 23, 23' are electronic circuits comprising integrators as measured value memories which store the current values of the adjacent ultramicroelectrodes 3, 3'. In said portions 23, 23', a signal for effecting an integration is supplied over addressing lines 16, 17, and the ultramicroelectrodes are connected with the bias lines 20, 21. In said portions 22, 22', the output potential of an integrator is supplied to the measuring lines 18, 19 by signals of the addressing lines 14, 15.

In FIG. 5, a CMOS well 24 comprising a source 25 and a drain 26 is integrated in silicon 1s as a planar carrier. Together with CMOS aluminum 27, a gate and paths of polysilicon 31 connect the chip-internal elements in the CMOS dielectric 28. Also by aluminum, the source 25 is electrically connected with a gold electrode 30 through a liquid-sealed silicon nitride passivation 29. In a crossing portion 32, for example paths like the addressing line 15 cross with a measuring line 18 according to FIG. 4.

Preferred Arrangements

For constructing the electric sensor array, planar carriers or substrates of different materials are used. Silicon is a particularly favorable material, since due to the usual technological methods of semiconductor production, the ultramicroelectrode arrays according to the invention may be produced in thin film technology and in wafer processes. Said method is variable and inexpensive, when array positions having a low density, i.e. substantially 10 to 30 array positions per electric sensor array, are to be produced, so that the ultramicroelectrodes are connected with contact surfaces at the edge of the chip over insulated direct contacts, as it is illustrated in FIG. 1.

When additional electronic elements like transistors, diodes, resistances and capacitors are integrated for addressing individual positions of the sensor array for controlling and switching as well as reading out the individual positions, such as illustrated in FIGS. 3 and 4, silicon technology is very favorable. Silicon as a planar carrier element is particularly also used when more than substantially 60 array positions per sensor element or a very dense arrangement of said positions is to be realized.

For a direct electric contacting, the use of glass and glassy substances as well as ceramic and also the particularly different types of polymers as planar carriers is suitable. All substrates must have the property that metallic paths and structured ultramicroelectrodes may adhesively be applied on them. The semiconducting silicon is insulated by thin layers of silicon dioxide or silicon nitride or mixtures thereof. The ultramicroelectrodes and, if required, auxiliary electrodes or auxiliary metallic surfaces are applied to the individual positions of the electric sensor element by evaporation or sputtering of precious metal films like gold, platinum or iridium, and usually structured by photolithographic processes and/or wet- or dry-etching. By thin adhesive layers of chromium or titanium or tantalum or other similar metals, the adhesion of said precious metals to the planar substrate is improved. In particular embodiments, nm-structured ultramicroelectrodes are included in the insulating layers and planarized therewith for the purpose of high chip yields and short-circuit stability.

The ultramicroelectrodes used for detection according to FIG. 2 are arranged at least in pairs and may be arranged as interdigital annular structures 3a, 3a', 3b, 3c, as interdigital structures of different geometries 3, 3', 3d, 3d', 3g, 3g' in an individual or a multiple design or even as a meander 3i, 3i'. They can be used together with surfaces of disc-shaped ultramicroelectrodes as well as in combination with auxiliary electrodes in a very wide range of combinations.

The strip-shaped electrode structures, which are provided in pairs as circular or spiral-shaped or interdigital or meandering arrangements are preferably used as a detection method for the redox recycling and produced photolithographically in dimensions between 200 nm and 800 nm, but in principle, they are suitable in both larger and smaller dimensions.

Similar electrode structures having a structural width of below 500 nm, preferably between 100 and 300 nm, are produced by impedance spectroscopy, for a marker-free detection of the affinity-binding of large molecules to the electrode-linked catcher molecules.

The strip-shaped electrode structures, which are provided in pairs as circular or spiral or interdigital or meander-shaped arrangements, are preferably used in redox recycling as detection methods and photolithographically in dimensions between 200 nm and 800 nm, but in principle, they are suitable in both larger and smaller dimensions.

Similar electrode structures having a structural width of below 500 nm, preferably between 100 and 300 nm, are produced by impedance spectroscopy for a marker-free detection of the affinity-binding of large molecules to electrode-linked catcher molecules.

A particular property of pairs of strip-shaped ultramicroelectrode structures and also of additional electrodes positioned very closely thereto is the generation of high electric fields having a field strength of up to several megavolt per m and relatively low potentials of typically 0.5 to 20 V. Electric fields between sub-µm electrodes only extend in the immediate vicinity of the electrodes and therefore preferably penetrate the molecule layers with which said electrodes are covered, but they cover comparably little of the surrounding electrolyte solution.

This in turn permits to realize an electrophoretic transport of molecules at potentials of a few volt only and thus, a considerably lower potential is required compared to so-called macroelectrodes, having dimensions of typically more than 10 µm. Disturbing processes, like electrolysis, pH-gradient production, a. o., which are caused by higher potentials are also reduced or avoided by this method.

Figure 2A:
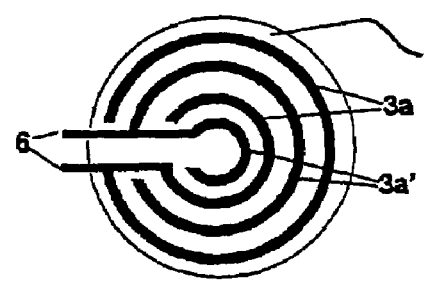
FIG. 2 show arrangements and combinations of different forms of ultramicroelectrodes and auxiliary electrodes of an individual array position.
Figure 2B:
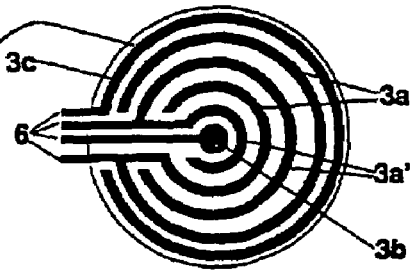

When arranging a plurality several pairs of ultramicroelectrodes as shown in FIG. 2b, an optional field-production between the different electrodes is provided. The possibility of differential and bridge circuits in an electrochemical detection process also provides measurement technical advantages for compensating interferences. Thus, the two pairs of interdigital ultramicroelectrodes which are illustrated in FIG. 2d, having different geometries are suitable for differentiating circuits due to different detection properties, such as the amplification rate in redox recycling.

Different organic loads also serve the purpose of a difference measurement. By covering a pair by galvanic deposition of metals not producing self-assembling monolayers, as for example nickel or the like, an immobilization is prevented. Also a subsequent individual removal of the immobilization layer on an electrode, e.g. by desorption of a self-assembling layer by electric oxidation on one of said electrode pairs, may be used for difference measurements of said type.

Figure 2C:
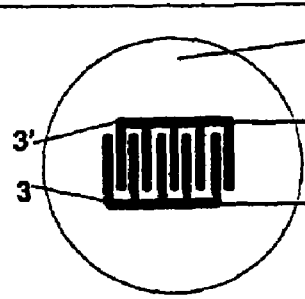
Figure 2D:
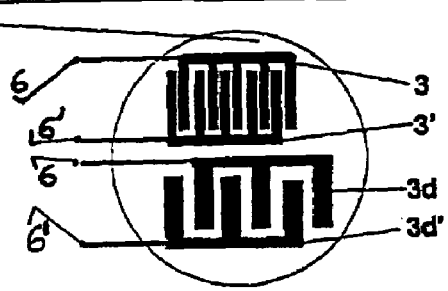
Figure 2E:
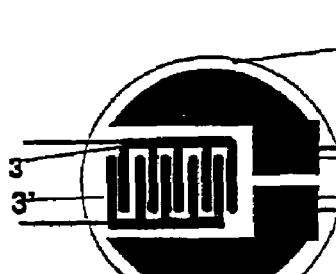
Figure 2F:
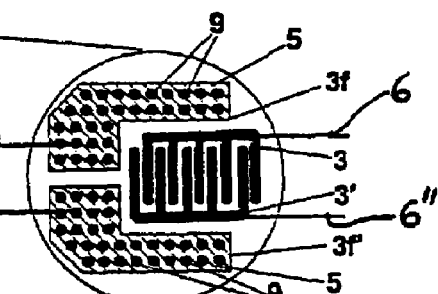
Figure 2G:
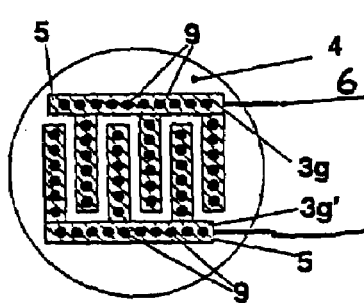
Figure 2H:
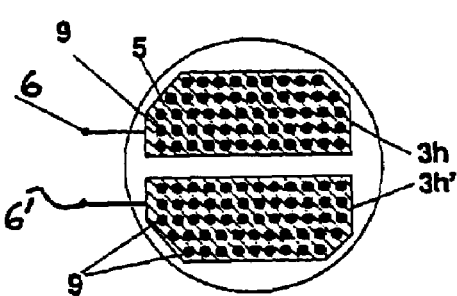

The production of dot-shaped ultramicroelectrodes 9 having a size of 1 to 2 µm on the arrays insulated in the remaining surface, such as illustrated in FIGS. 2f, 2g and 2h, provides an optimum hemispheric diffusion of electrode-active particles to the electrode surfaces. Said hemispheric diffusion provides a current density per surface which is more than 10 times as high at said dot-shaped electrodes, both, in a detection and in an application of electric fields, compared to macroelectrodes.

In a particular embodiment, said dot-shaped electrodes as well as the strip-shaped electrodes according to FIGS. 2a, 2b, 2c, 2d, 2e, 2f, 2h and 2i may be covered by a thin insulating layer on one or on both electrodes of a pair and therefore represent a particular measuring element for a capacity measurement of immobilized molecules or molecules linking to the surface. In the same way, a difference measurement is provided by such an insulation of one of two pairs of ultramicroelectrodes.

A combination of a pair of ultramicroelectrodes with two-dimensional auxiliary electrodes, such as illustrated in FIG. 2e, is used for enlarging metallic linking surfaces for the immobilization of molecules. Simultaneously, said surfaces like 3e and 3e' may also be used for an application of additional electric fields, e.g. for transporting molecules close to the detection electrodes 3 and 3', or for providing a field support when removing undesired molecules. In FIG. 2f, a combination of an interdigital ultramicroelectrode pair with auxiliary electrodes 3f, 3f' is shown, which are provided by the described dot-shaped electrodes. The different properties of said ultramicroelectrodes which have been described above for strip-shaped and dot-shaped electrodes are combined.

In a particular embodiment, such as illustrated in FIG. 2h, planar electrodes having ultramicroelectrode-shaped dots 9 are particularly used for impedance spectroscopy. Immobilized molecules may be specifically linked above the entire electrode surfaces or in the interspaces or on active electrode surfaces. In another embodiment, the molecules are immobilized on the above-described thin insulating layers above said electrodes.

Other combinations of electrode shapes and thus of their properties, like for example a double arrangement of electrode pairs 3, 3' or a combination of 3a, 3a' with 3e, 3e' or 3e, 3e' with 3g, 3g' and others are possible.

The annular ultramicroelectrodes 3a, 3a' in FIGS. 1, 2a and 2b are a particular embodiment, said electrodes in principle showing similar properties as the pairs of interdigital microelectrodes 3 and 3', but allow a more effective use of the sensor array surface and an application of central 3b and outer auxiliary electrodes 3c, which are important for field distribution and field production. By the latter arrangement, a cage-like field over e.g. intermittently inactive electrodes 3a, 3a' may be produced, and molecules may selectively be drawn into said field or repelled.

Figure 2I:
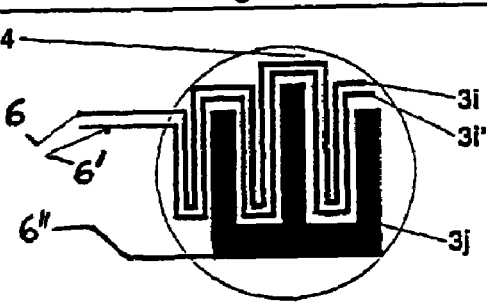

As far as their properties are concerned, the meander-shaped electrodes 3i and 3i' illustrated in FIG. 2i correspond to the annular and interdigital strip electrodes, and may also be combined with auxiliary electrodes 3j for difference measurements or for field production.

A special type of strip-shaped electrodes, which is not shown in the illustrations, is a spiral arrangement of the ultramicroelectrodes in which parallel electrode strips extend from the outside to the inside or from the inside to the outside and lead to separate contacting paths. Said spiral ultramicroelectrodes may also be provided in multiple combinations as pairs having different geometries, if required also comprising additional auxiliary electrodes, either in a planar shape or corresponding to 3b and 3c.

Both, the annular and the circular and spiral ultramicroelectrodes may additionally be structured with dot-shaped ultramicroelectrodes similar to FIG. 2g, then also having similar properties.

According to claim 7, a particular embodiment of ultramicroelectrode arrays is provided by multiply stacking strip-shaped electrodes, as shown in FIGS. 2a, 2b, 2c, 2d or 2i, or planar electrodes similar to FIG. 2e one upon the other, then insulating said electrodes with respect to each other by intermediate insulating layers like silicon dioxide, silicon nitride, siliconoxynitride. For this purpose, evaporation of metals and PECVD deposition of the insulating layers is combined. Said stacked electrodes have a thickness of typically 10–200 nm and act as ultramicroelectrodes at the cut edges of such a stack which is covered by an insulating material, realizing a maximum approach of the electrodes and a production of ultra high field strengths. In said arrangement, the individual layers are individually laterally uncovered to contact surfaces from below an insulating cover layer.

In principle, it is also possible to combine the ultramicroelectrodes and auxiliary electrode structures as shown in FIG. 2 and described above with metallic surfaces which do not have an electric connection. They then serve e.g. as areas for immobilizing affinity-binding molecules.

The ultramicroelectrodes of an individual array position are provided with metallic total surfaces of typically 100–30 000 $\mu m^2$ and therefore allow a construction of array positions having very small dimensions, the distances of the array positions typically corresponding to the dimensions of the active electrode surfaces of 30 $\mu m$ to 300 $\mu m$, but can also be substantially larger or smaller if so required by the applications.

As shown in FIG. 1d, the array positions are separated from each other by volume separating micro compartment walls 8 for special applications like particularly quantitative voltammetric measuring methods such as the redox recycling. In case of a qualitative detection, such as a local impedance spectroscopy at sensor-linked catcher molecules, a volume separation is usually not required.

Microareas having volume compartments are also used for effecting reactions and molecule immobilizations on individual array positions. If required by the detection, said compartments may optionally be removed after having effected said immobilization reactions. Thus, an ideal planar sensor array is provided, which is homogeneously accessible for both, analyte and reagent solutions.

The molecules to be immobilized may also be locally positioned on sensor positions without compartments by printing, piezo or ink jet methods or other spotting methods, like micro capillary dosage.

The catcher molecules to be immobilized are linked to the surfaces of the planar carrier elements, such as for example silicon dioxide, glass, ceramic or polymers or to the walls of the Si or polymer microcompartments by usual methods over bifunctional reagents, e.g. alkyloxysilane having different functional groups like halogen, amino, thioester and aldehyde groups, succinimide, carbodiimide and other usual coupling groups [H. G. Bäumert and H. Fasold, Methods in Enzymology, vol. 172, p. 584].

A preferred immobilization embodiment is the use of a gold and platinum surface as an immobilization area for thiol derivatives of catcher molecules, providing so-called self-organizing molecular monolayers on said well defined electrode surfaces [S. D. Evans et al., J. Amer. Chem. Soc. 113 (1991) 5866].

According to another embodiment, the array positions completely coated by self-assembling layers on the electrodes are again partly cleaned. Molecules which were immobilized together on the metallic surfaces, both on detection and on auxiliary surfaces, may selectively be desorbed from the detection electrodes by application of electric fields. A desorption of thiols is obtained by electric potentials, so that coatings are removed from the detection electrodes. They may then detect products which are for example provided on other surfaces of the sensor position, such as the metallic auxiliary surfaces.

Alternatively to the immobilization of affinity-binding molecules on the electrodes or auxiliary electrodes or metallic auxiliary surfaces or the walls or the inorganic sections of the individual sensor areas as described above, said affinity-binding molecules may optionally be positioned above said sensor positions and for this purpose linked to particular or gelatinous carriers. In this form, the products of the enzyme markers of biochemical assays, which are linked to spherical or particle-shaped polymers or metallic or mineral particles, may be arranged in the above described microcompartments or mechanically fixed, for example by inclusion. Fixing magnetic carrier particles by magnets in said microcompartments below the chips is also suited for charging different sensor positions.

Gels with incorporated affinity-binding molecules or molecule complexes may also be introduced into said microcompartments between walls 8 or over the entire sensor surface. Like in a gel electrophoresis, such gels may usually be charged with biochemical assays or assay components by diffusion or electrically supported diffusion. In contrast to other described methods, this can be effected independently at each individual sensor position by arranging several ultramicroelectrodes at each array position.

According to a particular embodiment, the molecules immobilized at the sensor surface are covered by a diffusible hydrogel partially in the compartments or homogeneously over the entire sensor surface. The gel acts as a protective layer or facilitates the molecule transport by electrophoresis.

The arrangement of immobilized biochemical assays at particles or in gels above the electrodes is realized by detection methods, such as the redox recycling, measuring the low-molecular enzyme products produced by said assays and diffusing at the electrodes, as long as the inclusion of water in said gels or interspaces between particles allows a diffusion. The redox recycling itself is characterized in that due to small distances between the ultramicroelectrodes, surface-mounted particles or gels do not affect such detection, since they extend preferably in or close to the molecular double layer being provided at the electrode surfaces by polarization. In the same manner, an impedimetric detection at the ultramicroelectrodes is substantially particle-independent in contrast to usual methods which use electrodes that are far distant from each other [V. M. Mirsky et al. Biosensors & Bioelectronics 12, 9–10(1997) 977]. In ultramicroelectrodes having an electrode distance of 200 nm and DNA molecules with a length of substantially 1 $\mu m$, which at the surface of said electrodes are affinity-bound very closely with respect to each other, the electric field between 2 strip electrodes substantially extends through the molecules themselves, further distant particles as well as the basic electrolyte in the solution only having a reduced influence.

An individual control of electrochemical processes for a detection at each individual array position is effected independently by not affecting said processes by an electric readout and a switching (addressing) related thereto. An electrode polarization, such as it is required for example for the voltammetric redox recycling, is individually provided at all sensor positions. This may be effected without any problem simultaneously and in parallel by multipotentiostats having direct conducting paths to each chip array position and each individual electrode, compare Hintsche et al., Biosensors & Bioelectronics, 9(1994) 697. The number of possible sensor positions being limited by the electronic expenditure of the measuring appliance and also by the number of conducting paths, the individual detector electrodes are measured serially, i.e. consecutively. The electric polarization potentials for the anode and the cathode are maintained in the redox recycling process even when the electrodes are connected to a measuring device over integrated measuring lines on a sensor chip individually one after the other or in groups (lines or columns) by individual switches.

In the most simple embodiment comprising a direct contacting of the electrode positions according to FIG. 1, an ASIC 35 "off chip" is used for this purpose. As far as the measurement is concerned, said ASIC has the functionality of a multiplexer, i.e. the sensor positions 4 which are individually connected with the ASIC are addressed serially (consecutively) and supplied to one single bipotentiostat 34 for being read out. The individual switches of the multiplexer are not provided as on-off-switches, but as changeover switches. In a non-addressed (non-readout) state, they connect the sensor positions with a bias potential serving for maintaining the electrode polarization during the non-readout-state. This is illustrated in FIG. 6. In said figure, the same switching states are marked as described before according to FIG. 3, so that this figure is self-explanatory. The potentiostat comprises a reference electrode and a counter electrode (Ref and Aux), the use of which electrodes is known. The only unilateral microelectrodes WE1, WE2, WE3 to WEn correspond to the electrodes 3 of FIG. 3. The multiplexer 10 corresponds to the addressing control, and the switched-on state corresponds to the addressed state our readout state, in which WE1 is coupled to the readout line 18 over an activated switch 12. All other sensor positions are connected to the potential for electrode polarization by switched-off switches 12 and switched-on switches 13, said potential being supplied to line 21. A circuit 35 is not provided in the area of the sensor positions, but outside of the carrier 1.

According to a more complex embodiment, an interference-free changeover in a serial addressing process of a larger array of sensor electrodes, as illustrated in FIG. 3, is achieved by arranging additional lines 20, 21, which are supplied with a potential, with bias potentials E, F or potential E–F at a carrier 1, in addition to the usual addressing and measuring lines, such as they have been used for a long time in electronic storages. The addressing is effected by an addressing unit 10 over addressing lines 14/15 and 16/17, which addressing unit may be arranged outside of the real electric sensor array in FIG. 3. The measuring lines 18 and 19 in FIG. 3 and the bias lines 20 and 21 are read out by special reading amplifiers 11, which are also positioned outside of the real electric sensor array. All electrodes 3 of the different sensor positions are recorded line by line and measured individually by said parallel measuring lines 18, whereas the parallel measuring lines 19 may record and individually measure all interdigital electrodes 3' line by line according to FIG. 3. All electrodes 3 are supplied with the same polarization voltage E by said bias line 21, which voltage is for example required for the oxidation of a type of molecules to be detected. In the same way, all electrodes 3' may be supplied with a potential F for the electrode polarization by said bias line 20, said potential being required for a reduction.

The alternating or changeover means 12 and 13 (as 12, 12' and 13, 13') integrated at each sensor position 4 provide a changeover between a readout and a non-readout state. In the readout state, the electrochemical reaction in process of a sensor position is recorded by measurement technical methods over a pair of measuring lines 18, 19 and simultaneously controlled by a multipotentiostat. In the non-readout state, the electrochemical processes, e.g. oxidation or reduction, are continuously supplied with polarization voltages and controlled by bias lines 21 for 3 and 20 for 3', said lines being arranged in parallel and at a distance of said sensor positions.

The switch elements 12, 12' and 13, 13' are locally arranged in silicon wafers at each sensor array position 4, for example by conventional CMOS technology, usual semiconductor technology. Above said integrated CMOS switches, to which the measuring, bias and addressing lines are connected, a liquid-resistant insulating layer, e.g. of siliconoxynitride, optionally in combination with silicon-dioxide is provided. The contact between the switch elements 12 and 13 and the individual electrodes 3 and 3', which are applied on said insulating layer by electron beam evaporation or sputtering and similar processes by thin-film technology as described, is provided by a perpendicular through-contacting to the CMOS element plane in the silicon. All structures above said liquid-resistant insulating layer correspond to the details illustrated in FIGS. 1 and 2, with the difference that there is no direct contacting by conducting paths as shown in FIG. 1. A changeover from the readout to the non-readout procedure or state for the inter-digital ultramicroelectrodes is realized without influence by a particular construction of the integrated CMOS switch elements 12 and 13. This is the necessary prerequisite for the entire measurement technical process, since at the electrode surface, an electrochemical double layer is produced by electrode polarization, said layer having to be preserved as a sort of chemical memory during the switching procedure.

The alternating procedure lasts only micro seconds, so that during this period of time, locally present electrode capacities 33 act as potential storages. Thereafter, the supply of the electrodes is changed over from the measuring lines 18 and 19 to the bias lines 20 and 21 with a polarization voltage.

In FIG. 3, the black complete circles 12, 12' represent those switch elements, which in the readout state, are supplied with a polarization voltage by said measuring lines 18 and 19, and which are connected by said lines with reading amplifiers for detecting an electrochemical, voltammetric or impedimetric event. The electronic element 10 is addressed column by column so that several sensor positions 4 are in a readout state, as schematically illustrated. They may be read out by a measurement technical element comprising reading amplifiers 11, and the electrochemical process may be controlled, said readout being effected subsequently by one reading amplifier or in parallel by two or more reading amplifiers. The column-by-column addressing by parallel pairs of addressing lines 14, 15 allows an optional extension of said sensor positions addressed as a column and an optional number of elements, which may again be measured subsequently by parallel pairs of measuring lines 18, 19 or in parallel by reading amplifiers. After terminating a measuring procedure at said perpendicular column of sensor positions, illustrated by black switch elements, an adjacent perpendicular column comprising switch elements 13, 13' so far inactive may be switched to the measuring position as described before by the subsequent pair of addressing lines 16, 17, controlling electrodes 3 or 3'. This happens after switching the column, which has been in the readout state before, to the non-readout state. Proceeding in this manner, each sensor position may be addressed and read out individually or in columns. Said measuring, bias and addressing lines may be realized on the silicon plane by a multilayer wiring, as it is usual in silicon technology for electronic storage components.

A detailed illustration of the measuring, bias and addressing lines is given in FIG. 3*a* by an array extracted from a sensor position 100. In FIG. 3, only one operational illustration was selected, whereas in FIG. 3*a*, all possible switching states which the array 100 may adopt are indicated. Two electrodes 3,3' with their supply paths 6,6' and a through-contacting 12*a*,12' are positioned centrally. An addressed state is illustrated in which the electrodes 3,3' are coupled to measuring lines 19,18 over switch elements 12,12'. Said measuring lines conduct the potential of the microelectrodes out of the sensor array and make it accessible for the measuring unit 11. Non-activated switches 13,13' which are also marked and relate to the same array 100 are indicated by broken lines. They are activated only when the addressing lines 14 and 15 change their switching state, so that the switches 12,12' switch off and the switches 13, 13' simultaneously switch on. When the latter switches couple said electrodes 3,3' from said through-contactings 12a,12a' to conservation paths 20,21 also extending in parallel, a new direct coupling of the electrodes to a conservation potential is provided without an interruption of the potential supply having occurred.

The addressing lines 14,15 are addressed by a column addressing unit 10 such that one column of sensor positions is always in an addressed state with switched-on switches 12,12', whereas all remaining sensor positions are switched off by inverted signals on the lines 16,17 of FIG. 3. The lines 16,17 functionally correspond to the lines 14,15, but they are marked with another reference numeral for the operational illustration of FIG. 3; they activate the switches 13,13' and deactivate the switches 12,12'.

The lower part of FIG. 3a is a schematic illustration of a circuitry, said illustration showing a switched-on state with closed switches 12,12', whereas the switches for providing a conservation potential 13,13' are open. The addressing lines 14,15 are inverted once at the sensor position, so that both switching states are always present complementarily, and an alternation of the switching state of the addressing line provides a changeover of the switch position of pairs of switches 12, 13 and 12',13', each forming an alternating switch.

The alternating switches described here are also used in FIG. 4 following hereinafter, but at first, the comprehension of the alternating switches shall be dealt with more in detail with reference to FIGS. 8,8a. Said figures shall be explained with reference to FIG. 3 and to the enlarged alternating switches at sensor position 100 and to FIG. 3a. The sensor position 100 is shown in the upper part of FIG. 8, a sensor position 101 is shown in the lower part of FIG. 8. Symbolically, FIG. 8 would have to be turned by 90°, so that the lines 18,21 as one of the bias lines and one of the measuring lines would correspond with the figures of identical designation of FIG. 3 as far as their orientation is concerned. Accordingly, FIG. 8 only shows the left contact arm of sensor position 100 and the left contact arm of sensor position 101, thus an addressed state and a non-addressed state characterized by a conservation potential. The individual switch elements which are used for a changeover shall be explained shortly. An addressing line 14 and a parallel addressing line 16 are shown, said lines having different potentials. A logical "zero" on said addressing line 14 causes CMOS transistors 50,53 to be switched on, one of said transistors being adapted as a p-channel and one as a n-channel transistor for being able to conduct current in both directions. Transistors 52, 51 do not have a logical switching function, but only serve for compensating interferences in switching.

The transistors 50 to 53 form a capacity-compensated switch 33, corresponding to said function 12.

By said marked logical zero at the addressing line, the n-channel transistor 50 and also the p-channel transistor 53 receive a switch-on signal "1". Thus, the potential of line 18, which is designated D here, is contacted or coupled through to the microelectrode 3 at a connecting path 6.

A pair of CMOS transistors 40,41 represents the other switch 13, which is switched-off here. The connection of the gate is adapted such that in case of a logical zero on line 14, said switch 13 is blocked. When the potential changes, the switching state of the two switch elements 12,13 changes as shown in the lower part of FIG. 8. Here, a logical "1" on the addressing line 16 (according to FIG. 3) causes transistors 40',41' of said switch 13 to switch on and provide a bipolar current direction, so that a conservation potential E on a line 21 is contacted through to a connection 6 of an electrode 3'. At said switching state of line 16, two transistors 50' and 53' block for adopting a non-addressed state.

When regarding FIG. 8a, the switching state becomes clearer, an array position 100 being marked in said figure and both microelectrodes 3,3' being controlled by alternating switches. Said illustration corresponds to the schematic illustration of FIG. 3a, only being generalized insofar as said switching configuration is valid for all array positions (sensor positions) 100,101,102,110,111,112 of FIG. 3 (and also of FIG. 4). Corresponding allocations of bias lines 20,21, measuring lines 18,19 and addressing lines is clearly visible by the marked reference numerals, when also referring to FIG. 3, so that a detailed explanation of FIG. 8a which results from FIG. 8 and FIG. 3 as well as FIG. 3a shall not be given here.

In another specific embodiment which is schematically illustrated in FIG. 4, integrated elements for reading out, amplification and, if required, for a temporary storage are additionally provided at the sensor positions besides the CMOS switch elements 12 and 13. The readout state is determined by the addressing lines 14, 15 in the same manner as described above with respect to FIG. 3, and the remaining sensor positions are controlled with respect to their potential by the addressing lines 16, 17 over bias lines 20 and 21 and read out by measuring lines 18, 19. Electronic amplifiers are arranged at each sensor position and at each individual electrode 3 and 3' in the electronic elements 22,22' and 23,23' of FIG. 4. An electrochemical measuring signal which is generated by electrode processes is amplified by pre-amplifiers directly at the sensor position and may then be read out in an addressed state over a pair of measuring lines 18, 19 in accordance with FIG. 3. According to this method, the non-addressed reading amplifiers in the electronic elements 23,23' of the parallel adjacent columns are without function.

In a particular embodiment, storage means are additionally integrated in said electronic elements 22, 22' and 23, 23'. The electrochemical process also occurring at time intervals at which sensor positions are in a non-readout state, said time intervals are used for accumulating and storing the signal generated in the ultramicroelectrodes over the reading amplifiers of the elements 23, 23' e.g. in an electronic temporary storage means. According to said embodiment, the signal generated at the electrodes is supplied to a temporary storage means over reading amplifiers, said temporary storage being read out over the measuring lines in a later reading procedure. In a readout procedure, the electrochemical result accumulated in the storage means during the complete non-readout state is read out very quickly.

In said arrangement, it is not necessary to accept longer measuring times during a readout procedure of a sensor position 4. This kind of (hidden) achievement of measured values and temporary storage is provided by the particular construction comprising additional bias lines. By said method, a considerable acceleration of the readout process and a substantial improvement of the utilizable signal is achieved. In the embodiment according to FIG. 4, electric sensor arrays having a higher density of the array positions (1000 and more) may be arranged due to an integration of electronic components at the individual sensor positions.

Typically for the integrated CMOS switches and the additional electronic elements below the array positions in the silicon, standard transistors, as schematically shown in FIG. 5, are arranged as CMOS wells 24 comprising sources 25 and drains 26. Gates and conducting paths of polysilicon 31 connect chip-internal elements, like CMOS aluminum 27 in the CMOS dielectric 28. The contacting of the chip-internal elements with the electrodes at the sensor array positions is also obtained by aluminum or tungsten through a liquid-dense silicon nitride passivation 29. A crossing section 32 exemplarily shows, how conducting paths cross, e.g. an addressing line 15 and a measuring line 18 according to FIG. 4.

The above described electric sensor arrays which are equipped with different electronic elements, are all suited for a multi analyte measurement. As described before, an immobilization of different affinity-binding molecules is provided on individual sensor array positions, e.g. in microcompartments, by adding reaction solvents by micro dosage, e.g. ink-jet-like dosing method (e.g. piezodosing means) or micro capillary dosage. It is also possible to individually apply molecules on individual positions by printing methods, said molecules then reacting or adhering. Self-assembling layers are for example transferred from a printing device to an electrode surface by so-called contact printing and thus individually coated over a thiol gold bond.

In another embodiment, an immobilization is obtained by microflow systems or printing means for the application of liquids through inlet and outlet openings over individual array positions or in groups or in rows. All embodiments of array positions thus equipped with different affinity-binding molecules, are then brought into contact as a whole with a multi analyte mixture. This may be realized by immersion of the sensor array into said analyte solution or by incorporation into a flow cell or by filling compartments at the individual positions. Due to their high specificity, the different affinity-binding molecules on or above the array positions exclusively bind their target molecule, insofar as said target molecule is present in the analyte mixture. Said binding procedure as well as a similar binding procedure at immobilized molecules in gels or on particles is a prerequisite for a subsequent electrochemical detection process. By using carrier-bound catcher molecules, a high charging density is achieved in a sensor array position, not only the surfaces, but also the volume being used.

Enzyme markers are used for a redox recycling, said enzyme markers being either introduced into the sensor array position by the target molecule or linked by secondary binding procedures, like antibody linkage, intercalation, covalent adhesion and other usual marking reactions after a specific linkage has occurred. Said marker enzymes, which are only present at array positions, at which a molecular detection reaction has occurred, are impregnated with an electrochemically inactive substrate, e.g. p-aminophenylphosphate which is then transferred to an electrode-active product, the p-aminophenol, by an enzyme reaction. In a cyclic process of an oxidation and a reduction occurring at an anode and cathode of strip-shaped ultramicroelectrodes, an accumulated current is determined, said current strictly correlating with the quantity of molecules bound at said array position. In relation to the bound analyte molecules, the quantity of introduced marker enzymes has to be quantitative and stoichiometric. When using the microcompartments provided for immobilization also for a volume separation in this kind of detection, the concentration of electro-active species occurring in each microcompartment is a quantitative dimension for the number of individual detection reactions occurred at said array. Therefore, the absence of an electrochemical reaction also means the absence of a detection event and thus the absence of the searched analyte at a respective array position.

The electrode active molecules produced by the enzyme markers for the redox recycling, may diffuse without problem to the electrode surface in aqueous gels. They also diffuse from a particle package above an electrode array through the liquid between solid particles, a concentration increase being provided particularly rapidly in a small remaining volume.

The detection process, due to the ultramicroelectrode behavior, occurring only directly at the electrode surface, the decisive zone is the electrode double layer and a few molecule layers above said layer. Therefore, said method is exclusively determined by a molecular movement according to Braun, independently of a convection, so that active stirring is not necessary, and stop-flow methods or closed chambers and microcompartments may be used.

In another embodiment, when the microcompartments have been removed after immobilization, only qualitative statements regarding the presence or absence of analytes are obtained, provided that the convection of developing marker enzyme products is sufficiently suppressed, e.g. by a sufficient distance of the positions and a stopped flow analysis.

In a further embodiment, planar sensor positions for a redox recycling detection are again provided with volume-separating elements for the sensor positions. This may for example also be realized by applying printing means as described above with respect to immobilization. By said method, individual sensor positions, groups of sensor positions or lines of sensor positions may separately be recorded and measured.

In another embodiment using electrochemical impedance spectroscopy as a detection method, the arrangements of electronic switch and additional elements with alternating current described in FIGS. 1, 3 and 4 are also used. Due to the specificity of said measuring method and the distance of the electrodes in the nm dimensions, a marker-free measurement of such a reaction is provided.

For effecting measurements, alternating currents having certain frequencies or frequency mixtures of 0.1 Hz to 1 MHz are supplied to a bias potential of preferably 10–200 mV, said potential being supplied to the electrodes of the sensor positions in the same manner as the electrode polarization for voltammetric methods. In said detection method, electrode distances of <500 nm, preferably 20–200 nm, are used. Similar to the embodiments for redox recycling, the affinity-binding molecules immobilized on or between electrode surfaces in a sensor array position are combined with a mixture of different analytes, and the molecular detection reaction occurs as described above. Due to strong electric fields of several MV/m achievable by said small electrode distances it may be measured individually at each position, how the affinity-binding molecules cover the electrode surface. This is shown by a decrease of the ultramicroelectrode capacity subject to the covering of the surfaces. The success of the immobilization and the covering degree may be observed quantitatively by said method. The individual sensor array positions provided with affinity-binding catcher electrodes are individually measured by impedance spectroscopy, the capacity, the conductivity and the dielectric constant as well as the phase angle being separable by the measurement and its evaluation. After a detection reaction at an individual array position having occurred, said reaction usually taking place with a larger biomacromolecule, a large molecule complex is formed, said complex typically being larger than a distance between two electrodes. The electric field does not considerably reach beyond said molecule complexes, thus only including the portions close to the electrodes, so that floating particles do not disturb. A new impedance measurement after a detection reaction, said measurement using the same parameters, is used for a difference determination. An evident change informs about the positions at which complex linkages have occurred. The impedance modification is caused by a displacement of the electrolyte and an interference of the electric field, e.g. by charged DNA molecules.

As distinguished from quantitative redox recycling, the impedance spectroscopic detection method is semi-quantitative and allows a statement about molecular detection reactions having occurred or not. The parameters which are evaluated by impedance spectroscopy allow statements about the size of the molecules which have linked at the electrode surface in a detection reaction, and about the charging state of said molecules. The density of molecule coating also influences the measuring result. All parameters may be considered in a more detailed analysis of the molecular detection process and the partners involved.

In a particular embodiment, an electric sensor array is covered with a hydrogel after immobilization of the affinity-binding molecules or after a molecular detection reaction and corresponding washing processes have occurred. Said covering with a hydrogel may be advantageous for different methods of using the electric sensor array. When covering the surface-linked affinity-binding molecules with a hydrogel, the analytes may be introduced into the gel or approached to the affinity partners or added by diffusion processes actively by dosage or electrophoretically by application of electric fields by auxiliary electrodes. The coating with hydrogels after a molecular detection reaction at the surfaces may also be used for approaching additional markers or reagents to the molecule complexes and for detecting them by electrophoretic processes or direct dosage.

Alternatively, hydrogels are used for including particle-linked immobilized catcher molecules or immobilized target analytes after a molecular detection reaction in the microcompartments. Said method is preferably suited for an application of redox recycling, since the gel does not substantially prevent the diffusing enzyme products from getting to the electrode surface. Only a deceleration of the diffusion is to be observed.

In another embodiment, the hydrogels are applied evenly over the entire electric sensor array, providing an improved allocation of binding processes to individual array positions by inhibiting diffusion, without microcompartments having been produced.

Besides being used for the detection processes themselves, the electrodes arranged at the individual sensor positions, and planar auxiliary electrodes or auxiliary electrodes provided with dot-shaped electrodes, as well as the strip electrodes arranged in spiral or circular shape according to FIG. 2 may also be used for an application of electric fields in the sense of a free-field or gel electrophoresis. For transporting charged analyte molecules or reagents to the electrode surfaces, e.g. to the position of a molecular detection reaction, interdigital ultramicroelectrodes according to FIGS. 2b, 2c, 2d or 2g, which are arranged in parallel, may particularly advantageously be used. According to an embodiment of said method, the two ultramicroelectrode pairs of FIGS. 2b, 2c and 2d are for example connected to an electrophoretic system such that two interdigital finger pairs or pairs of strip-shaped ultramicroelectrodes belonging together form a pole of the electric field. Depending on the polarization and the charge of the molecules, electrophoretic transport processes are initiated. When using fields having a low frequency in the lower Hz and mHz range, molecules are reciprocally transported to the electrodes. Usually, the electric fields are generated in sequences. In the currentless intervals, gases obtained by electrolysis may diffuse and pH gradients may balance.

In another embodiment, auxiliary electrodes as in FIGS. 2e and 2f are used for an application of the electric fields described before. They may have an identical polarization and be connected against an interdigital electrode pair 3, 3', or a field is produced between the auxiliary electrodes 3e and 3e' or 3f and 3f, to attract the molecules close to the detection electrodes 3, 3'. In contrast to the planar auxiliary electrodes 3e and 3e', the auxiliary electrodes 3f and 3f, having dot-shaped active electrode surfaces with an ultramicroelectrode character, allow a substantially higher current density per surface due to an improved diffusion. A substantially higher current density per surface compared to the electrodes 3 and 3' may also be achieved by an electrode construction 3g and 3g'. Said dot-shaped structuring, due to a hemispherical diffusion, provides the advantage that a substantially higher current density per surface may be achieved despite the active electrode surface being reduced.

Said embodiment for transporting or approaching analyte or reagent molecules to the electrode surfaces is supplemented by a simultaneous use of detection and auxiliary electrodes for producing electric fields after a detection reaction has occurred. According to said method, considerable field strengths between the electrodes, which are already obtained at a low potential of less than 1V, are used for removing weakly linked molecules from their affinity partner by the detection electrodes, in contrast to stronger linked molecules. A simple "pair of interdigital ultramicroelectrodes" 3, 3' according to FIG. 2c allows a removal of weaker and therefore not correctly linked molecule complexes. The field applied between the electrodes 3 and 3', which is an alternating field of low frequency (a few Hz to MHz), is used for removing undesired species from both electrodes. Said low frequency alternating field causes an electrode which is charged for immediate charging of the undesired molecule to repel the molecule due to its high field. The two electrodes are subsequently put into said repelling state by the alternating fields, and the reaction occurs in an accumulated result on both interdigital systems. After a short time, i.e. a few tenths of a second to a few seconds, the field application is interrupted by stops during which gases and pH-modifying species may diffuse. The reaction may be supported by biochemical washing processes or by temperature modifications. A temperature control may be realized both, externally and by a heating means provided on the chip, said heating means being made of thin film metal strips, like platinum.

An application of the process as described for FIG. 2a is possible for each pair of interdigital or strip-shaped ultramicroelectrodes by using electrode arrangements according to FIGS. 2b, 2d, 2e, 2f and 2i. In principle, said method may be used by combining optional detection and/or auxiliary electrodes with the same method of low-frequency pole reversal and removal of weakly-binding or undesired molecules from the electrode surfaces.

According to a particular embodiment, the electrodes which are located at an outer position in FIGS. 2b, 2e, 2f and 2e, are used for field production, whereas the electrodes positioned between them are currentless. This type of application may also be used for transporting molecules to the intermediate electrode pairs since said electrodes are positioned in a kind of field cage. Moreover, the same multiple arrangements allow combined direct current and alternating current applications, pole reversals as well as an optional addressing of the individual electrodes, selective effects of a molecule transport to and a molecule removal from optional electrodes thus being achieved.

In the embodiments according to FIGS. 2e and 2f, the planar or dot-shaped auxiliary electrodes may be used such that a desired polarity of the electrodes to one or to both ultramicroelectrodes is provided for removing molecules. In this respect, a direct current or a crosswise low-frequency alternating current application, e.g. in FIG. 2e between the electrodes 3e and 3' or 3e' and 3 is possible. Thus, the individual electrodes may be treated selectively. A different treatment of the electrode systems according to FIGS. 2b, 2d, 2e and 2f may be used according to another embodiment for removing undesired bonds at individual electrodes and for maintaining them at others, so that conclusions with regard to the difference quantity may be drawn from the difference measurement.

The above described methods for using electric fields are particularly suited for the circular electrodes according to FIG. 2b or for similar spiral structures by applying a kind of field cage through a center electrode over the electrodes located therebetween, so that they may be used by said field in the desired manner also in a currentless state for removing or approaching molecules.

According to another embodiment, a dot-shaped electrode arrangement according to FIG. 2h may advantageously be used for both a concentration and a removal of molecules. For this purpose, said electrodes are arranged at different positions of a sensor array, e.g. as an external ring or concentrated at an internal position or by combination of both selected positions of a sensor array. They serve for producing strong fields at other array positions over the space of the sensor array by particularly high current density. The high current density achievable at comparably low potentials produces field cages which particularly improve the transport of charged molecules according to electrophoretic principles.

EMBODIMENTS

EXAMPLE 1

Production of an Electric Sensor Array with Direct Output Contact in Silicon Technology Microelectrode structures according to FIGS. 1 and 2a are produced by standard silicon technology, compare Reimer et al., Sensors and Actuators, A 46/47(1995) 66. A thermal oxide of a thickness of 500 nm is produced on 4" silicon wafers. On said oxide, a photo resist is photolithographically structured such that the contours of the electrodes are uncovered for the electrode structures. An ultramicroelectrode system of concentric rings according to FIG. 2a comprises annular electrode strips having a width of 1.5 µm and an ring distance of 800 nm. The rings are alternately connected with the contacts according to FIG. 2a via conducting paths 6. 16 sensor positions are arranged on the sensor array in a 4×4 matrix with array positions of a diameter of 300 µm. 2×16 output contacts are arranged on two adjacent sides of a silicon chip having a size of 1×1 cm. The distances of the sensor array positions are 400 µm so that an active area of substantially 2.5 mm×2.5 mm is provided.

The oxide is etched to a depth of substantially 150 µm by immersing it into a 10% hydrofluoric acid during 15 sec. An adhesive titanium layer having a thickness of 20 nm and a gold layer having a thickness of 150 nm are evaporated by electron beam onto the entire surface. All the material between the electrodes, conducting paths and contacts is removed by a liftoff process. Subsequently, the wafer is covered by a siliconoxynitride layer having a thickness of 400 nm, said layer being produced in plasma by chemical deposition (PECVD-SiN$_x$:H). Subsequently, the array positions and the external contact surfaces are uncovered by reactive chemical dry-etching. After centrifuging a protective varnish thereupon, the wafer is sawed in to a depth of substantially 250 µm from the backside according to the individual chip edges provided.

EXAMPLE 2

Production of an Electric Sensor Array with a Direct Contacting on Glass

Interdigital electrode arrays according to FIG. 2e, having 9 sensor positions are structured in a 3×3 matrix on 4"-Pyrex-glass-wafers by a photolithography according to example 1. Unlike example 1, an adhesive chromium layer of a thickness of 20 nm, followed by a platinum layer of a thickness of 150 nm are evaporated onto the glass and finally structured by a lift-off method according to example 1. As an adhesion agent for the subsequent insulating layer, a 3% solution of alkyloxysilane in acetone is brought into contact with the surface. After centrifuging a polyimide layer of a thickness of 10 µm thereupon, the sensor array positions, which have a size of 400 µm and are positioned at a distance of 500 µm with respect to each other, are structured by a standard photolithography such that the contact surfaces and the sensor positions are uncovered. An interdigital electrode system with auxiliary electrodes according to FIG. 2e comprises 90 fingers at each electrode finger system, each finger having a length of 200 µm and a width of 1 µm, the interdigital distances being 0.9 µm. As illustrated in FIG. 2e, the auxiliary electrodes 3e and 3e' have a planar design up to a distance of 50 µm from the edge of the sensor array position. As in example 1, the wafer is protected and sawed in.

EXAMPLE 3

Production of an Electric Sensor Array System with CMOS Switches

A switch plane is produced by a CMOS standard method, compare Widmann, Mader, Friedrich, Technologie hochintegrierter Schaltungen, Springer Verlag Berlin 1996, in a process with 1 µm minimum structures. Crossings of conducting paths required according to FIG. 3 are realized by crossovers 32 of polysilicon paths 31a and aluminum paths 27. A higher electric resistance is not of importance due to small sensor currents. In the CMOS method used, switches 12, 12' and 13, 13' are advantageously adapted as transmission gates. A transmission gate connects the points 12a, 12a' with line 18 and 19, and the points 13a, 13a' with bias line 21 and 20. Addressing lines 14, 15, 16, 17 comprise a pair of conducting paths extending in parallel, at which signals of a complementary polarity are supplied to the gates of the two transistors of a transmission gate. Alternatively, an on-chip inverter may produce two complementary signals from an addressing line at each sensor position for complementarily contacting the transmission gates 12, 13. In one polarity, the transmission gate from 12a to 18 is conductive and the transmission gate from 12a to 21 is blocking (switching state 12). In a reverse polarity, 12a-18 is blocking and 12–21 is conductive (switching state 13). The transmission gates switch both, positive and negative currents.

In addition to the usual connecting pads of a CMOS circuit at the edges of a chip, the circuit according to FIG. 3 comprises aluminum pads at positions 12a, 12a' and 13a, 13a' by which pads a connection to the electrode arrays is provided. Usually, the CMOS process is terminated by applying a PECVD nitride layer and opening the connecting pads in said passivating layer. By an identical liftoff method as described in embodiment 1, an adhesive layer and gold electrodes 30 are directly evaporated onto said insulating layer and photolithographically structured as described above. A further passivation is not provided, the contacts of the interdigital and auxiliary electrodes being conducted directly perpendicularly into the switch plane located thereunder.

EXAMPLE 4

Production of an Electric Sensor Array Comprising Switches, Amplifiers and Integrator by CMOS Technology For producing the embodiment according to FIG. 4, an identical CMOS standard method and identical electrodes and path arrangements are used as described according to example 3. Said components are arranged at a surface of 300 µm×400 µm by using 1-µm-technology. Between the electrodes and the transmission gates leading to the measuring lines 18, 19, an operation amplifier is positioned and an integrated capacity of 1 pF connecting the output with the access of the operation amplifier. Further, a switch is positioned in parallel with respect to said capacity. Additional control lines lead from an addressing unit 10 to said switch, said control lines keeping said switch closed outside of the measuring intervals. In the described embodiment, a current of 1 nA generates a voltage of 1 V after 1 msec at the electrodes at the output of the operation amplifier. As described in example 3, said voltage is supplied to the measuring lines 18, 19 by transmission gates and measured by a reading amplifier 11.

EXAMPLE 5

Structuring Microcompartments with Prefabricated Polymers

Electric sensor arrays, which were produced according to examples 1 to 4, are liberated from protective varnish in an ultrasonic bath using acetone, and washed with alcohol and highly purified water several times. In a subsequent step, they are provided with microcompartments by laminating a polypropylene film onto them, said film having been perforated prior to lamination and having a thickness of 400 µm. The perforation corresponds to the sizes of the sensor array positions and the contact surfaces at the outer edges. Lamination is effected by inductive heating using heat-sealing technology. The film, which is applied by a vacuum printing means, said film having the size of the wafer, is adjusted by an optical control using adjusting marks on the wafer surface. The wafer, which is cooled down to −10° C., is broken along the pre-sawed chip edges, so that individual chips are obtained.

EXAMPLE 6

Structuring Microcompartments with Photolithographically Structured Polymers

Electric sensor arrays, which were produced according to examples 1 to 4, are liberated from protective varnish in an ultrasonic bath using acetone, and washed several times with alcohol and highly purified water. Subsequently they are coated with a Teflon AF film (DuPont) having a thickness of 15 µm by a spin-coating method. In advance, the entire wafer is wetted with the corresponding adhesive agent (DuPont). After baking the Teflon layer at a temperature of 150° C. during 20 minutes, the areas of the sensor positions and the contact pads are uncovered up to their metallic surfaces by reactive dry-etching. The wafer is broken along the pre-sawed chip edges, so that the individual chips are obtained.

EXAMPLE 7

Immobilization of Oligonucleotides on Electric Sensor Arrays

A chip produced according to example 5 and having polymer microcompartments of a height of 400 µm is mounted and wire-bonded by usual paths on a ceramic carrier. A reaction vessel having a diameter of substantially 5 mm is fixed on the chip by pasting a polymer molding of polysiloxane along the chip edges, said molding delimiting the active electrode areas. A solution of 5 mM 11-merkapto-undecanylamine in cyclohexanone is filled into said reaction vessel, covered and maintained at room temperature for 5 hours. The coating of the electrodes by self-assembling is controlled by an online-impedance-measurement (EG&G Model 398). The decreasing capacity due to said coating with a monomolecular molecule layer is a dimension for the cover. The coating is interrupted as soon as the original capacity of the chip electrodes has decreased by 70%.

Said coating of the metallic surfaces may alternatively be effected prior to breaking and individualizing the chips, by immersion of the entire wafer, from which the varnish has been removed previously, into similar solutions.

The surface of the chip, derivatized by amino functions, is subsequently subjected to an incubation with a drop (0.1–10 µl) 20 mM toluene-2,4-diisocyanate (TDI) in acetic acid ethyl ester (EEE) at room temperature during 10 to 60 minutes. EEE is used for washing and drying.

After washing a chip activated by said method with a neutral phosphate buffer solution, 5 nl 24mer oligonucleotide carrying a iodoacetyl group at the 5' chain end are consecutively introduced into each sensor array position by micro capillary dosing.

The nucleotide sequence is different at each array position depending on the different target DNA molecules to be analyzed. The volumes of the reaction liquids are smaller than the compartment volume. The coupling reaction occurs spontaneously during one hour at room temperature. After a covalent binding has occurred, the electric sensor array is washed with a SSPE buffer (0.9 M NaCl, 50 mM $NaH_2PO_4$, 5 mM $Na_2EDTA$, ph 7.5).

EXAMPLE 8

Affinity Binding of DNA on Electric Sensor Arrays with Carrier-Linked Oligonucleotides The analyte as a DNA mixture is charged to an electric sensor array charged with different catcher oligonucleotides according to example 7. Analyte DNA is used into which biotinylized primer biotin radicals were introduced by PCR during a conventional multiplication or reproduction of the DNA. The analyte DNA in SSPE buffer is transferred to a concentration of 1 µg/ml by a Denhardt's solution (0.5 g Ficoll, 0.5 g polyvinylpyrrolidone, 0.5 g RSA in 0.5 l $H_2O$) and charged to the sensor array and subjected to an incubation at room temperature for two hours. For removing excess analyte DNA, washing is effected at 40° C. with a SSC buffer (52.6 g NaCl, 26.5 g Na-citrate in 0.81$H_2O$).

EXAMPLE 9

Immobilization of Particle-Linked Affinity-Binding Molecules on Electric Sensor Arrays An electric sensor array, which was produced according to example 1 and provided with microcompartments according to example 5, is positioned above a usual magnet for handling magnetic carriers. 10 nl liquid suspensions of magnetic polymer pellets with different oligonucleotides are applied in each micro compartment by micro capillary dosing and fixed by the magnets at the bottom of the microcompartments above the electrodes. Charging of the magnetic carriers was effected in advance for all positions separately according to a standard method (Boehringer) by streptavidin/biotin coupling. The carriers are superficially coated with streptavidin and link the 5'-biotin-modified 24mer nucleotides. Over said streptavidin/biotin coupling, the different oligonucleotides are firmly immobilized on the magnetic carriers.

EXAMPLE 10

Detection of the Affinity-Binding on Surfaces of Electric Sensor Arrays

Electric sensor arrays with immobilized oligonucleotides according to example 7 are prepared for a readout by redox recycling after a hybridization in accordance with example 8. The entire electric sensor array is filled with 1.5 µl of a neutral phosphate buffer solution of the marker enzyme alkaline phosphatase, said solution being present as a streptavidin conjugation. The biotin/streptavidin linkage occurs during one hour. Thereafter, all non-linked enzyme conjugations are removed from the sensor surface by rinsing with 2 mM p-aminophenylphosphate in phosphate buffer pH 9.5. After sucking off any liquid salient with respect to the microcompartments, the p-aminophenol concentration which is produced in each micro compartment by enzyme reaction, and which is adequate to the quantity of twin-threaded bound DNA, is individually measured by a 16 channel multipotentiostat (own construction). For the redox recycling, the ultramicroelectrodes are charged in pairs with 2 different potentials. The anode with +350 mV and the cathode with −100 mV against a silver/silver chloride reference electrode (see FIG. 7). The anodic and the cathodic current of each array position is evaluated as an increase in current dI/dt at the respective sensor position. An increase in current of 0.5 to 2 nA per minute is obtained, depending on the charging density. The total of both currents is a quantitative dimension for the number of linked target DNA at each sensor position.

The quantity of linked DNA per sensor position is determined by using an array position of the sensor array as an internal standard. For this purpose, a 35mer oligonucleotide comprising 20 complementary bases with respect to the catcher oligonucleotide at an array position is admixed to the analyte in a known concentration.

EXAMPLE 11

Detection of the Affinity-Binding on Surfaces of Electric Sensor Arrays by Impedance Spectroscopy Electric sensor arrays which are structured according to example 6, are filled at each sensor array position with 10 nl oligonucleotide solution of a concentration of 10 µg per ml phosphate buffer pH 7. The 24mer oligonucleotides uniformly have 6 thymidine radicals at the 5' chain end, the last three of said radicals being modified by thiolate groups. The sulfur/gold linkage of the thiolate groups is finished after 12 hours.

Each array position is measured at room temperature by impedance spectroscopy (EG&G model 392) in a frequency range between 10 mHz and 1 MHz, and the complex impedance is analyzed.

The sensor array is washed with SSPE buffer (0.9M NaCl, 50 mM NaH2PO4, 5 mM Na2EDTA, pH 7.5). The analyte DNA in the SSPE buffer is transferred to a concentration of 1 µg/ml by a Denhardt's solution (0.5 g Ficoll, 0.5 g polyvinylpyrrolidone, 0.5 g RSA in 0.51$H_2O$) and applied onto the sensor array and subjected to an incubation during 2 hours at room temperature. For removing excess analyte DNA, washing is effected with an SSC buffer (52.6 g NaCl, 26.5 g Na-citrate in 0.81$H_2O$) at 40° C.

Each array position is again measured at room temperature by impedance spectroscopy in a frequency range between 10 mHz and 1 MHz, and the complex impedance is analyzed.

The difference of the measurements at each sensor array position before and after the DNA linkage indicates the position with the effected DNA linkage in case of a decrease of the electric conductivity term of the complex impedance.

EXAMPLE 12

Transport of Charged Molecules to Detector Electrodes of an Electric Sensor Array The analyte DNA in 200 mmol/l succinic acid buffer pH 5.1 is applied onto the sensor array in a concentration of substantially 1 µg/ml.

A current of 20 nA is supplied to all electrodes 3$e'$ and 3 during 80 msec with the help of an external precision current source. Subsequently, a changeover is carried out to the electrodes 3$e$ and 3' for 80 msec. The electrodes 3 and 3' have a positive polarity. The complete switching sequence is repeated 100 times. For removing excess analyte DNA, washing with a SSC buffer (52.6 g NaCl, 26.5 g Na-citrate in 0.81$H_2O$) is effected at a temperature of 40° C.

EXAMPLE 13

Electric Stringency Treatment of Hybridized DNA on Electric Sensor Arrays

An electric sensor array having a hybridized DNA, as used in example 12, is charged with a 200 mmol/l succinic acid buffer pH 5.1.

A 10 nA alternating current of 50 Hz current is supplied onto all electrode pairs 3, 3' during 0.2 sec. After an interruption of 0.2 sec, the entire switching sequence is repeated 100 times. Diffused, more weakly bound molecules are then removed by washing with a SSC buffer (52.6 g NaCl, 26.5 g Na-citrate in $0.81 H_2O$) at a temperature of 40° C.

EXAMPLE 14

Selective Desorption of Surface-Linked Molecules on Electric Sensor Array Chips An electric sensor array is produced according to example 1 and charged with oligonucleotides according to example 7. Electrode geometries according to FIG. 2e are used at the sensor array positions. pH 5.1 is filled into the sample ring.

All electrodes 3 and 3' on the sensor array are connected to a current source. Then, an alternating current of 20 Hz and a voltage of 2V is supplied for one second and again switched on after a stop of 0.5 seconds. Said sequence is repeated 50 times. Subsequently, the electric sensor array is washed with an SSPE buffer (0.9M NaCl, 50 mM $NaH_2PO_4$, 5 mM $Na_2EDTA$, pH 7.5).

The subsequent hybridization of analyte DNA only occurs on electrodes 3e, 3e' charged with catchers and is effected according to example 8.

Alkaline phosphatase is used for marking as in example 10. The electrodes 3 and 3' measure the p-aminophenol concentration produced at the surfaces 3e and 3e', said measurement being effected by redox recycling. The increase in current dI/dt is evaluated at a respective sensor position. An increase in current of 0.2 to 2 nA per minute is obtained, depending on the charging density.

EXAMPLE 15

Control and Recording of Measured Values by an ASIC

An electric sensor array is produced according to example 15, charged with oligonucleotide catchers and used for an affinity-binding of target DNA and a subsequent enzyme marking. A particularly developed ASIC for a serial electrode control comprising 32 switch outputs is connected to the 32 paths 6, 6' of the sensor array and connected with a bipotentiostat. The preparation and realization of the redox recycling are effected according to example 10. The anodic potentials of +350 mV and the cathodic potentials of –100 mV are supplied from the bipotentiostat to the ASIC and conducted to the individual sensor positions 4 over direct conducting paths. Each sensor position 4 is allocated to a switch system on the ASIC. Controlled by a processor, each sensor position is read out serially (consecutively) during 0.1 sec, said readout being controlled by the bipotentiostat. When alternating an array position from a readout state to a non-readout state, the anodic and the cathodic potential is switched to the respective bias line by the ASIC. Thereby, all 16 array positions operate continuously in redox recycling.

Said serial readout cycle is effected for 5 minutes. The increase of the accumulated current per time per array position is measured and interpreted according to example 10.

EXAMPLE 16

Control and Recording of Measured Values by Partly Integrated Electronic Means The addressing lines 14, 15 and 16, 17 of the sensor array, which are shown in FIG. 3, are connected with a PC-controlled decoder. A channel of an 8-channel multipotentiostat is connected to one each of the readout lines 18,19. The bias lines 20, 21 are supplied with an analogous anodic (+350 mV) and cathodic (–100 mV) potential, as in example 15.

Redox recycling is prepared and realized according to example 10.

In the readout state, all sensor positions in the column along the addressing lines 14,15 are activated and switched to the respective measuring channels of the multipotentiostat by integrated circuits 12, 12'. All other sensor positions are in the non-readout state and connected with the bias lines 20,21 by integrated circuits 13, 13', so that the corresponding potentials are also supplied to the electrodes 3, 3' and the redox reaction occurs continuously.

Each active sensor position is read out for 0.1 seconds by the multipotentiostat, said readout being processor-controlled. Subsequently, said column is switched to the non-readout state by said circuit 12, 12', using the decoder, and the next column is immediately addressed by the adjacent addressing lines.

Said readout cycle is effected for about 5 minutes. The increase in current per time is measured separately for each sensor position and stored in a PC. The evaluation corresponds to example 15. The recording is illustrated in FIG. 9.

EXAMPLE 17

Control and Recording of Measured Values by an Integrated Temporary Storage

An electric sensor array is produced according to example 4 and 5, the electrode geometries corresponding to those of FIG. 2c. The preparation of the electric sensor array with chemical components is effected according to example 15.

The addressing lines 14, 15 and 16, 17 of the sensor array, as shown in FIG. 4, are connected with a PC-controlled decoder according to example 15. To each of the readout lines 18, 19, a highly sensitive amplifier is connected with its output to an ADC. The bias lines 20, 21 are supplied with analogous anodic potential (+350 mV) and cathodic potential (–100 mV) from a bipotentiostat. Addressing is effected according to example 16.

Differing from said example, only the currents generated by redox recycling at the electrodes 3 and 3' in the non-readout state are stored individually for each electrode by integrated pre-amplifiers having internal integrators 23, 23'. When addressed in a later readout, only the content of said integrators is read out.

The redox recycling process occurring there generates current which is conducted to an internal position-specific integrator over an internal amplifier in a circuit 23 and accumulated there. The accumulation occurs during the entire non-readout state.

We claim:

1. An electrically controllable sensor arrangement comprising a plurality of arrays, each adapted for one of an electrochemical detection of molecular substances, transport and handling of charged molecules, wherein
more than two sensor positions are provided on a substantially planar carrier (1), each sensor position provided as an array (4) of at least two microelectrodes, to form more than two arrays;
a first guided wiring configured for electrically addressing the arrays (4) on said carrier (1), and a second guided wiring extending substantially perpendicular with respect to said first guided wiring;
wherein said first guided wiring allows for several sensor positions to be addressed by selecting at least one of row and column, for said addressed sensor positions to be read out substantially in parallel, but individually in an electric addressing procedure;
a further guided wiring attributed to said carrier (1), coupled to the sensor positions for transmitting measured signals from said addressed sensor positions;
an electrical control arrangement having said second guided wiring, for electric control at said more than two arrays (4), such that said arrangement continuously supplies a polarization voltage to arrays that are no longer addressed after terminating the electric addressing procedure as to addressed arrays effected via said first guided wiring, and the second guided wiring attributed to said carrier (1) is part of said electric control arrangement for sensor positions not addressed for a reading; said guided wirings for at least one of the following:
generating at least one of an electric direct field and alternating field at said arrays,
detecting different electrochemical reactions or properties individually at said arrays,
electrically reading out events having occurred at a sensor position between two electric addressing procedures of said same sensor position,
transporting affinity-binding molecules onto one of said arrays, to a particular carrier being present there or into a gel being present there, independent of optical properties, and for immobilizing said molecules there.

2. Sensor arrangement according to claim 1, wherein said planar carrier (1) comprises one of silicon, glass, ceramic and plastic.

3. Sensor arrangement according to one of claims 1 and 2, wherein an electrode surface of said microelectrodes (3,3a') comprises one of carbon and a precious metal film.

4. Sensor arrangement according to claim 1, wherein said first guided wiring allows for an individual electric addressing of each said array sensor position.

5. Sensor arrangement according to claim 1, having electronic circuits, wherein at each individual sensor position, microelectrodes are addressable by a respective one of said electronic circuits such that electrochemical events may be read out, and after said readout, potentials for an uninterrupted polarization are maintained, to not affect an electric double layer at microelectrodes wetted with a liquid.

6. Sensor arrangement according to claim 1, wherein integrated circuits are provided as changeover switches (12,13;12',13'), said integrated circuits being part of said arrangement for electric control (20,21;16,17).

7. Sensor arrangement according to claim 1, wherein electrochemical events are serially read out at least partly from said microelectrodes of an individual array (4) over time spaced intervals between individual addressing procedures of said array (4), providing measurements attributed to said individual array, for at least one of recording, storage and summing up.

8. Sensor arrangement according to claim 1, wherein said arrays (4) are controllable in electrically grouped groups via said first guided wiring (14,15;16,17), a respective group of arrays being individually controlled and comprising at least two arrays.

9. Sensor arrangement according to claim 1, wherein a measuring and storing unit (22,23;22',23') is associated with said at least two sensor positions, said measuring and storing unit being arranged to store measurements from said microelectrodes, representing the events at a time, prior to reading the measurements out electrically in a subsequent addressing step.

10. Sensor arrangement according to claim 1, for electrochemically detecting molecular assays and for transporting charged molecules, wherein surfaces of the microelectrodes and auxiliary microelectrodes are made of different materials.

11. Sensor arrangement according to claim 1, for electrochemically detecting molecular assays and for transporting charged molecules, wherein each individual sensor position comprises at least one pair of ultramicroelectrodes and wherein the ultramicroelectrodes have one of identical and different geometries.

12. Sensor arrangement according to claim 1, for electrochemically detecting molecular assays and for transporting charged molecules, wherein said microelectrodes are arranged in pairs as interdigital fingers, wherein the fingers are one of covered by dot-shaped microelectrodes and band structures, arranged in one of a spiral and a circular configuration.

13. Sensor arrangement according to claim 1, wherein said microelectrodes arranged in pairs comprise vertically stacked plural layers including band-shaped metal films separated by insulating layers.

14. Sensor arrangement according to claim 1, further comprising additional electrode surfaces besides said microelectrodes, arranged at said sensor positions and not showing microelectrodes behavior.

15. Sensor arrangement according to claim 1, for electrochemically detecting molecular assays and for transporting charged molecules, wherein said sensor positions are covered by liquids and wherein at least certain of said sensor positions may be supplied with one of reagents, analytes and mixtures of analytes.

16. Sensor arrangement according to claim 1, for electrochemically detecting molecular assays and for transporting charged molecules, wherein at individual sensor positions, affinity-binding molecules also having different specificity are immobilized on at least one of: said individual sensor positions; auxiliary metallic surfaces; surfaces of the carrier; and, compartment walls, for effecting one of voltage and resistance measurements using said microelectrodes.

17. Sensor arrangement according to claim 1, for electrochemically detecting molecular assays and for transporting charged molecules, wherein at individual sensor positions, affinity-binding molecules linked on said microelectrodes are removable by one of desorption and electrochemical oxidation.

18. Sensor arrangement according to claim 1, for electrochemically detecting molecular assays and for transporting charged molecules, wherein a voltammetric detection is effected using one of liquid analytes independent of particular components, surface-mounted gels, and adhering substances.

19. Sensor arrangement according to claim 1, for electrochemically detecting molecular assays and for transporting charged molecules, wherein an impedimetric detection is effected in liquid analytes independently of particular components.

20. Sensor arrangement according to claim 1, for electrochemically detecting molecular assays and for transporting charged molecules, wherein at each sensor position, individual molecular binding events are detected electrochemically after specifically linking analytes of mixtures of substances to said affinity-binding molecules immobilized at said sensor positions.

21. Sensor arrangement according to claim 1, wherein absence of molecular binding events is detected individually at each said sensor position, after analytes of mixtures of substances have formed a specific bond with said affinity-binding molecules immobilized at said sensor positions.

22. Sensor arrangement according to claim 1, wherein after analytes of mixtures of substances have formed a bond with said affinity-binding molecules immobilized at said sensor positions, individual molecular binding events are detected at each sensor position by using said microelectrodes by recording at least one of a quality and a quantity of redoxactive reaction products of binding-specifically introduced enzyme markers.

23. Sensor arrangement according to claim 1, wherein said individual sensor positions are separable by volume-separating compartments, for realizing a position-specific, quantitative electrochemical detection.

24. Sensor arrangement according to claim 1, wherein said microelectrodes comprise a precious metal and further comprising immobilization surfaces for self-assembling monolayers of different thiol-modified affinity-binding molecules on different sensor positions.

25. Sensor arrangement according to claim 24, wherein said self-assembling monolayers are formed by providing a similar coating with bi-functional thiol-modified molecules on all sensor positions, said molecules being used in a second reaction step for linking affinity-binding molecules at each individual sensor position.

26. Sensor arrangement according to claim 24, wherein said affinity-binding molecules immobilized at least at certain of said individual sensor positions of said electrically controllable sensor arrangement are coated with a layer of hydrogels.

27. Sensor arrangement according to claim 26, wherein said affinity-binding molecules immobilized at said individual sensor positions are coated with a layer of hydrogels, said hydrogels covering all of the arrays of the sensor arrangement.

28. Sensor arrangement according to claim 1, wherein different affinity-binding molecules are introduced into compartments at said individual sensor positions and fixed, and wherein the affinity-binding molecules are associated with one of polymers, nanoparticles of metals, mineral substances and gelatinous substances.

29. Sensor arrangement according to claim 1, wherein affinity-binding molecules are introduced at individual sensor positions and immobilized in a layer of hydrogels.

30. Sensor arrangement according to claim 1, further comprising an electric fields generator adapted for coupling between pairs of the microelectrodes associated with the electric sensor array, for moving charged molecules according to electrophoretic principles.

31. Sensor arrangement according to claim 1, further comprising an electric alternating fields generator coupleable to apply electric alternating fields for removing linked analyte molecules from said individual sensor positions depending on binding strength and charge.

32. Sensor arrangement according to claim 1, wherein a detectable effect is caused during said electric addressing procedure by said first guided wiring in said carrier, associated with said addressed sensor position (100).

33. Sensor arrangement according to claim 32, wherein a detectable effect is caused during an electric control by said second guided wiring in said carrier, associated with said non-addressed sensor positions.

34. Sensor arrangement according to claim 1, wherein said control arrangement comprises a direct link of said microelectrodes of said sensor positions to at least one potential (E, F) operable to supply current via the direct link.

35. Sensor arrangement according to claim 34, wherein said control arrangement comprises substantially loss-free direct lines from two microelectrodes (6,6'; 3,3') of a respective sensor position to a source of a potential difference (3,F) providing a current supply, and wherein said source of the potential difference is spaced from said sensor positions.

36. Sensor arrangement according to claim 1, wherein during an electric control, a detectable reaction is coupled at said non-addressed sensor positions to said second guided wiring in said carrier.

37. Sensor arrangement according to claim 1, wherein an alternating switch is attributed to each microelectrode of each array (4), for switching said electrodes (3,3') of said array between a guided measuring wiring (18,19) and said second guided wiring (20,21) for providing a conservation voltage as polarization voltage.

38. An electrically controllable sensor arrangement comprising a plurality of arrays (4), adapted for electrochemically detecting molecular substances and adapted for one of transporting and handling charged molecules, said sensor arrangement having
more than two sensor positions on a substantially planar carrier (1), each sensor position being provided as an array (4) of at least two microelectrodes;
a first guided wiring for electrically addressing each array (4) on said carrier (1) and for coupling at least one microelectrode selected from said microelectrodes to at least one measuring line (18,19), oriented substantially perpendicular to said first guided wiring;
a second guided wiring oriented substantially perpendicular to said first guided wiring, for supplying an electric polarization voltage, chargeable with current, to said arrays, wherein after terminating a respective addressing procedure, non-addressed arrays are substantially continuously supplied from the electric polarization voltage;
an alternating switch connected to each electrode of each array, for switching electrodes of a respective one of said arrays between a guided measuring wiring, thereby coupling to said guided measuring wiring for measurement, and said second guided wiring, thereby applying a conservation voltage from said polarization voltage.

39. A control method for a sensor arrangement comprising a plurality of arrays (4) of at least two microelectrodes each, said sensor arrangement being provided with a first arrangement for addressing each array on a carrier, comprising the steps of:
effecting an addressing procedure for reading selected ones of the arrays;
after termination of the addressing procedure, continuing to supply no longer addressed arrays with a substantially constant polarization voltage by an electric control; and employing said addressing procedure and said continuing to supply with said polarization voltage to the arrays for at least one of generating at least one of an electric direct field and alternating field at said arrays;

detecting different electrochemical reactions or properties individually at said arrays;

electrically reading out the events having occurred at a sensor position between two electric addressing procedures of said same sensor position; and transporting affinity-binding molecules onto one of said arrays, to a particular carrier being present there or into a gel being present there, independent of optical properties, and for immobilizing said molecules there.

40. Control method according to claim 39, comprising maintaining said substantially constant polarization voltage even when current loads occur at said no longer addressed arrays within a time interval of electric control.

41. Control method according to claim 39, wherein at least two switch functions are attributed to each array (4) as a sensor position, switching said array between a pair of measuring lines and a second guided wiring and provide a conservation voltage.

* * * * *